United States Patent [19]

Miyazawa et al.

[11] Patent Number: 6,013,198
[45] Date of Patent: *Jan. 11, 2000

[54] LIQUID CRYSTALLINE COMPOUND REPLACED BY FLUORINE CONTAINING GROUP, LIQUID CRYSTAL COMPOSITION, AND LIQUID CRYSTAL DISPLAY DEVICE

[75] Inventors: Kazutoshi Miyazawa; Shuichi Matsui; Tomoyuki Kondo; Takashi Kato; Yasuko Sekiguchi; Etsuo Nakagawa, all of Chiba, Japan

[73] Assignee: Chisso Corporation, Osaka, Japan

[ * ] Notice: This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 08/921,799

[22] Filed: Sep. 2, 1997

Related U.S. Application Data

[63] Continuation-in-part of application No. 08/698,177, May 15, 1996, abandoned.

[30] Foreign Application Priority Data

Sep. 11, 1995 [JP] Japan .................................. 7-258185

[51] Int. Cl.[7] .......................... C09K 19/30; C09K 19/12; C07C 19/08; C07C 22/00
[52] U.S. Cl. ............................... 252/299.63; 252/299.66; 570/129; 570/144
[58] Field of Search ........................... 252/299.63, 299.66

[56] References Cited

U.S. PATENT DOCUMENTS

| | | | |
|---|---|---|---|
| 4,871,469 | 10/1989 | Reiffenrathe et al. | 252/299.61 |
| 5,167,860 | 12/1992 | Sawada et al. | 252/299.63 |
| 5,171,469 | 12/1992 | Hittich et al. | 252/299.01 |
| 5,286,411 | 2/1994 | Rieger et al. | 252/299.63 |
| 5,292,454 | 3/1994 | Kurmeier et al. | 252/299.66 |
| 5,308,542 | 5/1994 | Poetsche et al. | 252/299.63 |
| 5,368,772 | 11/1994 | Rieger et al. | 252/299.63 |
| 5,516,454 | 5/1996 | Scheuble et al. | 252/299.01 |
| 5,534,189 | 7/1996 | Nakagawa et al. | 252/299.63 |
| 5,560,865 | 10/1996 | Nakagawa et al. | 252/299.01 |
| 5,578,241 | 11/1996 | Plach et al. | 252/299.01 |
| 5,616,284 | 4/1997 | Hittich et al. | 252/299.63 |
| 5,714,088 | 2/1998 | Miyazawa et al. | 252/299.63 |

FOREIGN PATENT DOCUMENTS

| | | |
|---|---|---|
| 0492668 | 7/1992 | European Pat. Off. . |
| 4414874 | 11/1994 | Germany . |
| 2266714 | 11/1993 | United Kingdom . |
| WO91/08184 | 6/1991 | WIPO . |
| WO91/10716 | 7/1991 | WIPO . |
| WO91/13850 | 9/1991 | WIPO . |
| WO91/16396 | 10/1991 | WIPO . |
| WO91/16399 | 10/1991 | WIPO . |
| WO92/14800 | 9/1992 | WIPO . |

*Primary Examiner*—C. H. Kelly
*Attorney, Agent, or Firm*—Wenderoth, Lind & Ponack, L.L.P.

[57] ABSTRACT

Liquid crystalline compounds are disclosed which compounds are expressed by general formula (1)

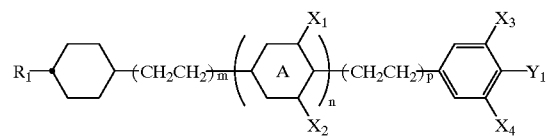

(1)

wherein $R_1$ represents an alkyl group having 1 to 10 carbon atoms, ring A represents 1,4-phenylene or 1,4-cyclohexylene, each of $X_1$, $X_2$, $X_3$, and $X_4$ independently represents hydrogen atom or fluorine atom, $Y_1$ represents $CF_3$ or $OCF_3$, and each of m, n, and p is independently an integer of 1 or 0. The liquid crystalline compounds have a wide temperature. The liquid crystalline compounds have a wide temperature range of nematic phase, low viscosity, large positive $\Delta\epsilon$, high chemical stability, high miscibility with other liquid crystalline compounds at low temperatures, small temperature dependency of viscosity and $\Delta\epsilon$, extremely high specific resistance (high voltage holding ratio), and good UV stability, and are preferably used for TFT. Also, disclosed are liquid crystal compositions containing the liquid crystalline compounds mentioned above, and liquid crystal display devices using the liquid crystal composition.

9 Claims, No Drawings

LIQUID CRYSTALLINE COMPOUND REPLACED BY FLUORINE CONTAINING GROUP, LIQUID CRYSTAL COMPOSITION, AND LIQUID CRYSTAL DISPLAY DEVICE

This application is a continuation-in-part of application, Ser. No. 08/698,177, filed Aug. 15, 1996 now abandoned.

TECHNICAL FIELD

The present invention relates to a liquid crystalline compound and a liquid crystal composition. More specifically, the present invention relates to a novel liquid crystalline compound replaced by a fluorine containing group, a liquid crystal composition containing the liquid crystalline compound, and a liquid crystal display device composed by using the liquid crystal composition.

BACKGROUND ART

Liquid crystal display devices are widely used for watches, desktop calculators, several kinds of measuring apparatus, panels for automobiles, word processors, electronic note-books, printers, computers, and televisions.

These liquid crystal display devices employ optical anisotropy ($\Delta n$) and dielectric anisotropy ($\Delta \epsilon$) of liquid crystal compounds. As display mode, dynamic scattering (DS) mode, guest-host (GH) mode, twisted nematic (TN) mode, super twisted nematic (STN) mode, thin-film transistor (TFT) mode, and ferroelectric liquid crystal (FLC) mode are known. As their driving mode, static driving mode, time sharing addressing mode, active matrix driving mode, and dual frequency driving mode are known. Among them, TFT mode is being paid public attention in particular.

While several characteristics are required of liquid crystal materials for TFT mode, the following three are considered to be necessary as common characteristics:

1) Temperature range of nematic phase of the liquid crystal materials is wide to such an extent that the materials do not cause the reduction in the temperature range of the nematic phase of a liquid crystal composition when the materials were added to a liquid crystal composition.
2) Viscosity of the liquid crystal materials is low including at a low temperature region.
3) Liquid crystal materials have a large $\Delta \epsilon$.

Among the characteristics mentioned above, 1) includes the requirements that the upper limit of the temperature of nematic phase is high and that the melting point of the liquid crystal materials is low so that the phase separation of the materials due to the precipitation of crystals hardly occurs even at a low temperature region.

Characteristic 2) is an extremely important factor to increase the response speed of oriented liquid crystal molecules to the electric field in a liquid crystal panel (Phys. Lett., 39A, 69 (1972)), and the increase in the response speed is most eagerly demanded at present to improve the quality of the display of liquid crystal compositions. At that time, small dependence on temperature of the response speed mentioned above, that is, small temperature dependence of the viscosity of materials and maintenance of a low viscosity of the materials even at low temperatures are considered to be important from the viewpoint that the deterioration in the quality of the display is not caused even at low temperatures.

Reasons why characteristic 3) is desired are as follows:

In order to actualize the reduction of power consumption and the production of a large image screen, the reduction of driving voltage is necessary. Driving voltage, particularly, threshold voltage ($V_{th}$) is a function of $\Delta \epsilon$ as expressed by the following equation $$V_{th} = k\sqrt{K/\Delta \varepsilon}$$

wherein k is a proportional constant and K is an elastic constant.

As will be seen from the equation shown above, compounds having a large positive $\Delta \epsilon$ is necessary for reducing power consumption.

In addition, a small temperature dependence of $V_{th}$ is desired even at low temperatures in particular in order to raise the quality of the display of liquid crystal compositions and keep it in a wide temperature range.

In order to respond to such requirements, the exploration for compounds having a large positive $\Delta \epsilon$ is being conducted. Among the compounds already discovered, trifluoromethylphenyl derivatives expressed by formula (a) proposed in Laid-open Japanese Patent Publication No. Sho 59-78129 and trifluoromethoxyphenyl derivatives expressed by formula (b) proposed in Laid-open WO Japanese Patent Publication No. Hei 2-501311 are known as examples of the compounds having particularly a large $\Delta \epsilon$.

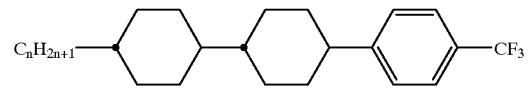

(a)

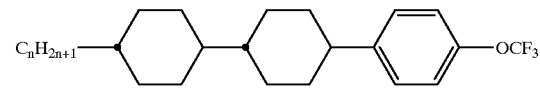

(b)

While these compounds have a three rings structure having $CF_3$ or $OCF_3$ at a terminal of the molecule, all of the bonding groups which link the three rings in a straight line are limited to a covalent bond. Based on this fact, in part, those compounds can not completely be said to fully satisfy required characteristics other than $\Delta \epsilon$.

Some of the compounds having $CF_3$ or $OCF_3$ at a terminal of the molecule are described in Liq. Cryst., 18 (4), 665 (1995), Laid-open WO Japanese Publication Nos. Sho 63-503226, Hei 3-503771, Hei 4-500214, Hei 4-500217, Hei 4-500682, Hei 4-501575, Hei 4-501576, Hei 4-507104, Hei 5-502676, and Hei 6-504032, DE Nos. 4004650 A1, 4013083, 4106345, 4108705 A1, and 4113053 A1, and EP Nos. 0439089 A1 and 0449288, in addition to the publications mentioned above. However, physical parameters of the compounds are not sufficiently described in those publications.

Further, the liquid crystalline compounds used in the liquid crystal compositions for TFT must be stable against external environmental factors such as moisture, air, heat, and light.

In order to develop characteristics required for particular display devices, liquid crystalline compounds are used in the form of a mixture of several or twenty-odd compounds. Accordingly, it is demanded that liquid crystalline compounds have a good miscibility with other liquid crystalline compounds, and a good miscibility even at low temperatures since the use environment of the compounds is expanded recently, in particular.

That is, liquid crystal compositions having a nematic phase particularly at low temperatures, precipitating no crystals, and developing no smectic phase are desired for the liquid crystal compositions for TFT in order to make it possible to use the compositions at a wide range of temperatures. Accordingly, liquid crystalline compounds having an excellent miscibility with other liquid crystalline compounds at low temperatures are particularly desired for the liquid crystalline compounds to be used in TFT.

TFT contains integrated nonlinear devices for switching particular image segments and is one type of active matrix mode liquid crystal displays which are considered to be suitable for high grade information displays such as for televisions, computers, automobiles, and airplanes. Liquid crystal compositions designed for such uses must have an extremely high specific resistance (high voltage holding ratio) and a good UV stability in addition to the large positive $\Delta\epsilon$ mentioned above. When liquid crystal compositions having no such characteristics were used, image contrast is decreased with the reduction of electric resistance in liquid crystal panels to raise a problem of "image sticking". Besides, there is a strong tendency of the liquid crystal compositions to shorten their utilization life particularly at the time of driving at a low voltage.

Liquid crystalline compounds similar to those of the present invention are disclosed in U.S. Pat. Nos. 4,871,469 and 5,292,454. However, the compounds disclosed in these patents are distinguished from the compounds of the present invention in their structure. Also, U.S. Pat. Nos. 5,286,411 and 5,516,454 described general formulas of liquid crystalline compounds which encompass some compounds of the present invention. However, the compounds of the present invention are not substantially disclosed in these patents. Besides, the compounds disclosed in these patents have, for example, a low clearing point or a poor capability of exhibiting nematic property compared with those of the present invention.

DISCLOSURE OF THE INVENTION

An object of the present invention is to dissolve the problems in the prior art mentioned above and to provide a liquid crystalline compound for TFT which satisfy required characteristics such as a wide temperature range of nematic phase, lower viscosity, larger positive $\Delta\epsilon$, high chemical stability, high miscibility with other liquid crystalline compounds at low temperatures, small temperature dependency of viscosity and $\Delta\epsilon$, extremely high specific resistance (high voltage holding ratio), and good UV stability at the same time, and to provide a liquid crystal composition containing the liquid crystalline compound.

As a result of the investigation by the present inventors, it has been found that a liquid crystalline compound provided with the characteristics mentioned above can be obtained by modifying liquid crystalline compounds so that the compounds have a trifluoromethylphenyl group or trifluoromethoxyphenyl group as example of known terminal substituent and, characteristically have a specific main skeleton at the same time, leading to the achievement of the present invention.

BEST MODE FOR CARRYING OUT THE INVENTION

In order to achieve the objects mentioned above, the present invention has the following aspects:

1. A liquid crystalline compound expressed by general formula (1)

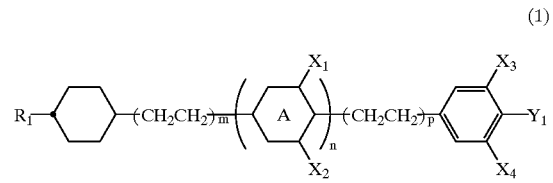

(1)

wherein $R_1$ represents an alkyl group having 1 to 10 carbon atoms, ring A represents 1,4-phenylene or 1,4-cyclohexylene, each of $X_1$, $X_2$, $X_3$, and $X_4$ independently represents hydrogen atom or fluorine atom provided that at least one of $X_1$ to $X_4$ is fluorine atom, $Y_1$ represents $CF_3$ or $OCF_3$, and each of m, n, and p is independently an integer of 1 or 0 provided that at least one of m and p is 1.

2. The liquid crystalline compound recited in the aspect 1 mentioned above wherein n is 0, m is 1, $X_3$ is fluorine atom, and $X_4$ is hydrogen atom.

3. The liquid crystalline compound recited in the aspect 1 mentioned above wherein n is 1, ring A is 1,4-cyclohexylene, both m and p are 1, and $X_3$ is fluorine atom.

4. The liquid crystal compound recited in the aspect 1 mentioned above wherein n is 1, ring A is 1,4-phenylene, m is 1, p is 0, all of $X_1$, $X_2$ and $X_4$ are hydrogen atom, and $X_3$ is fluorine atom.

5. The liquid crystalline compound recited in the aspect 1 mentioned above wherein n is 1, ring A is 1,4-phenylene, m is 0, p is 1, $X_1$ is fluorine atom, and $X_2$ is hydrogen atom.

6. The liquid crystal compound recited in the aspect 1 mentioned above wherein n is 1, ring A is 1,4-phenylene, m is 1, p is 0, each of $X_1$ and $X_3$ is fluorine atom, and $X_2$ and $X_4$ are independently hydrogen atom or fluorine atom.

7. A liquid crystal composition containing at least one liquid crystalline compound defined in any one of the aspects 1 to 6 mentioned above.

8. A liquid crystal composition containing, as a first compound, at least one liquid crystalline compound defined in any one of the aspects 1 to 6 mentioned above, and containing, as a second component, at least one compound selected from the group of the compounds expressed by any one of general formulas (2), (3), and (4)

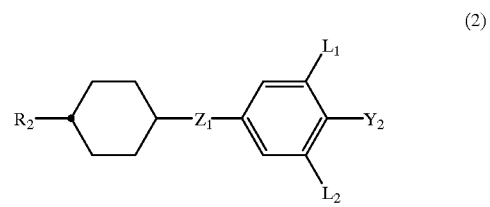

(2)

-continued

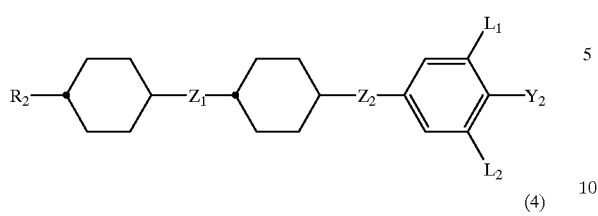
(3)

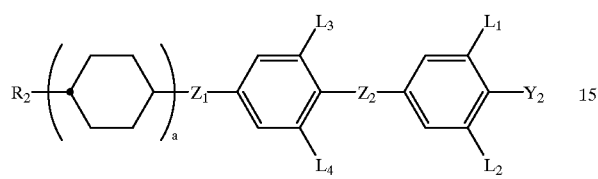
(4)

wherein $R_2$ represents an alkyl group having 1 to 10 carbon atoms, $Y_2$ represents fluorine atom, chlorine atom, $OCF_3$, $OCF_2H$, $CF_3$, $CF_2H$, or $CFH_2$, $L_1$, $L_2$, $L_3$, and $L_4$ represent, independently with one another, hydrogen atom or fluorine atom, $Z_1$ and $Z_2$ represent, independently with each other, $-(CH_2)_2-$, $-CH=CH-$, or a covalent bond, and a is 1 or 2.

9. A liquid crystal composition containing, as a first compound, at least one liquid crystalline compound defined in any one of the aspects 1 to 6 mentioned above, and containing, as a second component, at least one compound selected from the group of the compounds expressed by any one of general formulas (5), (6), (7), (8), and (9)

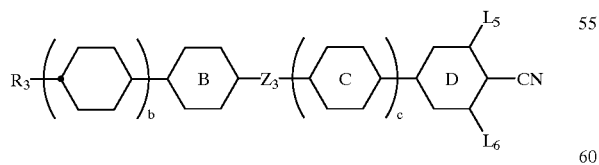
(5)

wherein $R_3$ represents fluorine atom, an alkyl group having 1 to 10 carbon atoms, or an alkenyl group having 2 to 10 carbon atoms, any methylene group in the alkyl group or alkenyl group may be replaced by oxygen atom provided that in no case two or more methylene groups are continually replaced by oxygen atom; ring B represents 1,4-cyclohexylene, 1,4-phenylene, or 1,3-dioxane-2,5-diyl, ring C represents 1,4-cyclohexylene, 1,4-phenylene, or pyrimidine-2,5-diyl, ring D represents 1,4-cyclohexylene or 1,4-phenylene, $Z_3$ represents $-(CH_2)_2-$, $-COO-$, or a covalent bond, $L_5$ and $L_6$ represent, independently with each other, hydrogen atom or fluorine atom, and b and c are, independently with each other, 0 or 1,

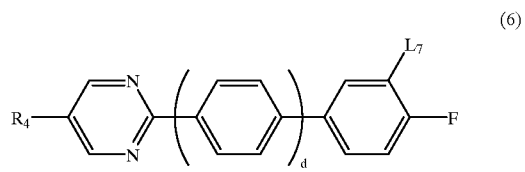
(6)

wherein $R_4$ represents an alkyl group having 1 to 10 carbon atoms, $L_7$ represents hydrogen atom or fluorine atom, and d is 0 or 1,

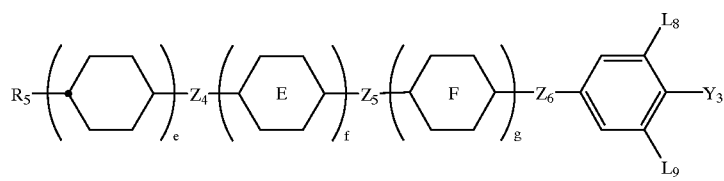
(7)

wherein $R_5$ represents an alkyl group having 1 to 10 carbon atoms, ring E and ring F represent, independently with each other, 1,4-cyclohexylene or 1,4-phenylene, $Z_4$ and $Z_5$ represent, independently with each other, $-COO-$ or a covalent bond, $Z_6$ represents $-COO-$ or $-C\equiv C-$, $L_8$ and $L_9$ represent, independently with each other, hydrogen atom or fluorine atom, $Y_3$ represents fluorine atom, $OCF_3$, $OCF_2H$, $CF_3$, $CF_2H$, or $CFH_2$ provided that when $Y_3$ represents $OCF_3$, $OCF_2H$, $CF_3$, $CF_2H$, or $CFH_2$, both $L_8$ and $L_9$ represent hydrogen atom; and all of e, f, and g are, independently with one another, 0 or 1,

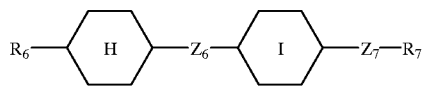
(8)

wherein $R_6$ and $R_7$ represent, independently with each other, an alkyl group having 1 to 10 carbon atoms or an alkenyl group having 2 to 10 carbon atoms, any methylene group in either the alkyl group and alkylene group may be replaced by oxygen atom provided that in no case two or more methylene groups are continually replaced by oxygen atom; ring H represents 1,4-cyclohexylene, 1,4-phenylene, or pyrimidine-2,5-diyl, ring I represents 1,4-cyclohexylene or 1,4-phenylene, $Z_6$ represents $-C\equiv C-$, $-COO-$, $-(CH_2)_2-$, $-CH=CH-C\equiv C-$, or a covalent bond, $Z_7$ represents $-COO-$ or a covalent bond,

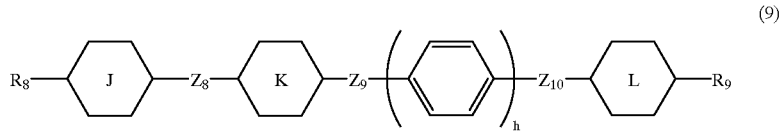

(9)

wherein $R_8$ and R represent, independently with each other, an alkyl group having 1 to 10 carbon atoms or an alkenyl group having 2 to 10 carbon atoms, any methylene group in either the alkyl group and alkylene group may be replaced by oxygen atom provided that in no case two or more methylene groups are continually replaced by oxygen atom; ring J represents 1,4-cyclohexylene, 1,4-phenylene, or pyrimidine-2,5-diyl, ring K represents 1,4-cyclohexylene, 1,4-phenylene one or more hydrogen atoms on the ring of which may be replaced by fluorine atom, or pyrimidine-2,5-diyl, ring L represents 1,4-cyclohexylene or 1,4-phenylene, $Z_8$ and $Z_{10}$ represent, independently with each other, —COO—, —(CH$_2$)$_2$—, or a covalent bond, $Z_9$ represents —CH=CH—, —C≡C—, —COO—, or a covalent bond, and h is 0 or 1.

10. A liquid crystal composition containing, as a first component, at least one liquid crystalline compound defined in any one of the aspects 1 to 6 mentioned above, containing, as a part of a second component, at least one compound selected from the group of the compounds expressed by any one of general formulas (2), (3), and (4) defined in the aspect 8 mentioned above, and containing, as other part of the second component, at least one compound selected from the group of the compounds expressed by any one of general formulas (5), (6), (7), (8), and (9) defined in the aspect 9 mentioned above.

11. A liquid crystal display device composed by using a liquid crystal composition defined in any one of the aspects 7 to 10 mentioned above.

Compounds of the present invention expressed by general formula (1) is characterized by having a specific skeleton comprising two or three rings including 1,2-ethylene group or 1,4-butylene group as central bonding group, and at the same time having known trifluoromethyl group or trifluoromethoxy group on the terminal phenylene group. These compounds can roughly be classified into two rings compounds expressed by any one of formulas (1-1) to (1-3) (first group); three rings compounds expressed by any one of formulas (1-4) to (1-7) central ring in which compounds is 1,4-cyclohexylene (second group); three rings compounds expressed by formula (1-8) or (1-9) in which compounds central ring is 1,4-phenylene group, and the bonding group linking the 1,4-phenylene group with terminal phenyl group is a covalent bond (third group); and three rings compounds expressed by any one of formulas (1-10) to (1-15) in which compounds central ring is 1,4-phenylene group, and the bonding group linking the 1,4-phenylene group with terminal phenylene group is 1,2-ethylene group (fourth group).

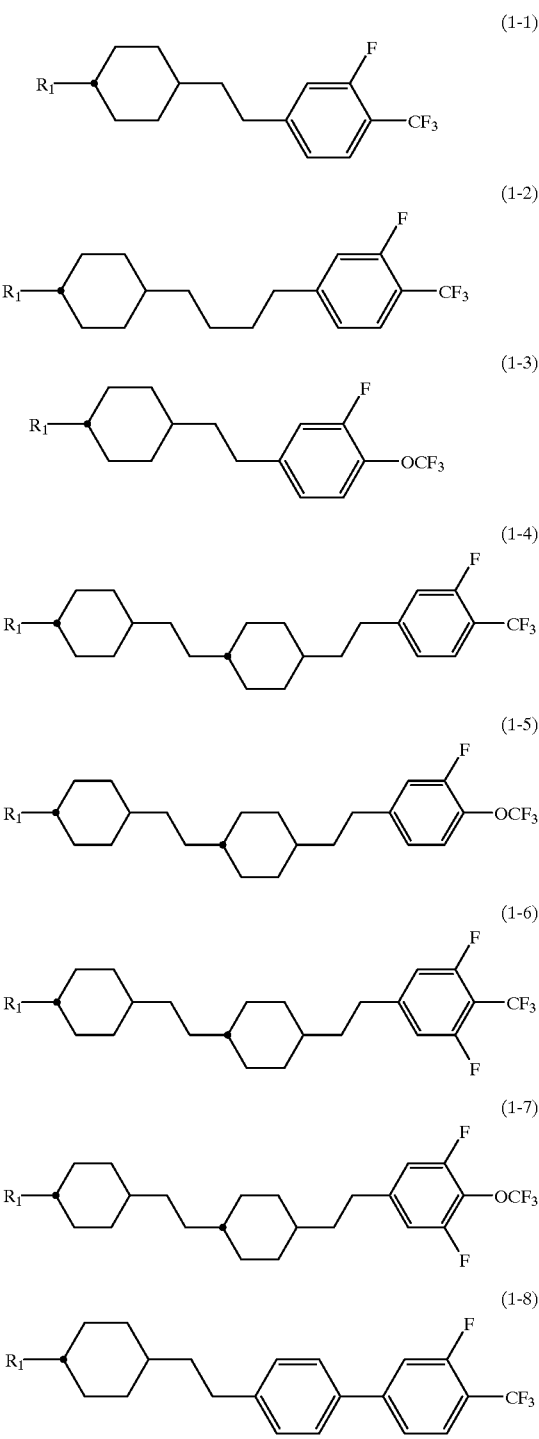

-continued

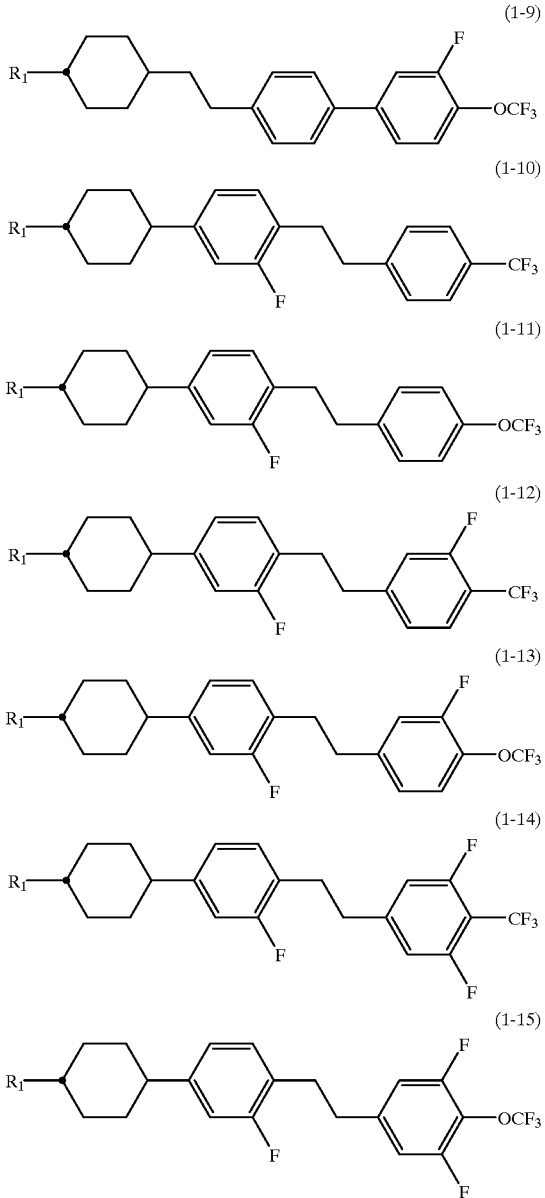

in each of the formulas, $R_1$ has the same meaning as mentioned above.

Any of these compounds of the present invention exhibit a wide temperature range of nematic phase, low viscosity, large positive $\Delta\epsilon$, high chemical stability, high miscibility with other liquid crystalline compounds at low temperatures, extremely high specific resistance (high voltage holding ratio), and high stability against UV and heat .and the dependency of $\Delta\epsilon$ and viscosity of the compounds on temperature is extremely low. Thus, the compounds are useful as the component for liquid crystal compositions for TFT.

Optical anisotropy ($\Delta n$) can optionally be controlled by suitably selecting $R_1$, ring A, $X_1$, $X_2$, $X_3$, $X_4$, m, n, and p in general formula (1) by which the compounds of the present invention are exhibited. For instance, it is sufficient to select compounds containing more 1,4-phenylene groups as ring A when a large $\Delta n$ is desired containing more 1,4-cyclohexylene groups as ring A conversely when a small $\Delta n$ is desired.

Among the compounds of the present invention, the ones included in the first group, mentioned above particularly exhibit a large positive $\Delta\epsilon$, low viscosity, and high clearing point, and thus the compounds are excellent as component of liquid crystal compositions.

Compounds of the second group particularly exhibit an extremely excellent nematic characteristics, and thus the liquid crystal compositions using the compounds as one of components exhibit such a preferable characteristic that the development of a smectic phase is not observed in the liquid crystal composition at low temperatures.

Compounds of the third group particularly exhibit a high clearing point and low viscosity, have a large positive $\Delta\epsilon$, are small in the viscosity increase at low temperatures in particular since the dependency of the viscosity of the compounds on temperature is small, and are excellent even in the miscibility with other liquid crystalline compounds, and thus the compounds are excellent as component of liquid crystal compositions.

Further, the compounds of the fourth group particularly exhibit a high clearing point and low viscosity, have a large $\Delta\epsilon$ and $\Delta n$, are small in the viscosity increase at low temperatures in particular since the dependency of the viscosity of the compounds on temperature is small, and beside, have a good miscibility with other liquid crystalline compounds, and thus the compounds are also preferable as component of liquid crystal compositions.

Compounds of the present invention are most preferably used as component for the liquid crystal compositions for TFT. However, since the compounds have such excellent characteristics as mentioned above, the compounds can preferably be used not only in such use but also in other uses, for example, for TN mode, STN mode, Guest-Host mode, and polymer dispersion type liquid crystal display deice, and as the liquid crystalline compound for dynamic scattering mode.

While the liquid crystal compositions provided by the present invention may be comprised only of the first component containing at least one liquid crystalline compound expressed by general formula (1), the liquid crystal compositions preferably contain, as a second component, at least one compound selected from the group of the compounds expressed by any one of general formulas (2), (3), and (4) mentioned above (hereinafter the compounds are referred to as second A component) and/or at least one compound selected from the group of the compounds expressed by any one of general formulas (5), (6), (7), (8), and (9) mentioned above (hereinafter the compounds are referred to as second B component), in addition to the compounds of general formula (1). Further, a known compound may be blended to the liquid crystal compositions as a third component for the purpose of adjusting threshold voltage, the temperature range of liquid crystal phase, $\Delta n$, $\Delta\epsilon$, and viscosity.

Among the second A component, the compounds expressed by any one of formulas (2-1) to (2-15), (3-1) to (3-48), and (4-1) to (4-53) can be mentioned as examples of preferable compounds included in the compounds expressed by general formula (2), (3), or (4).

(2-1) 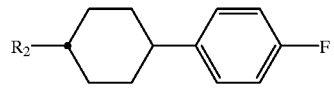
(2-2) 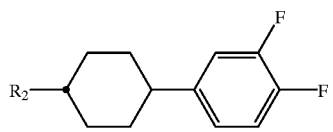
(2-3) 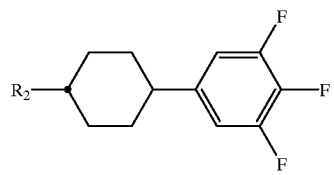
(2-4) 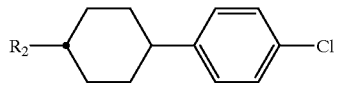
(2-5) 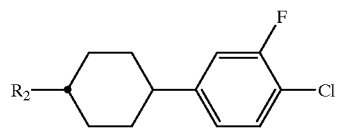
(2-6) 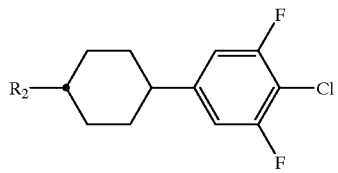
(2-7) 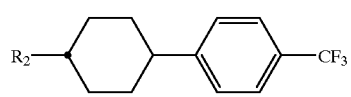
(2-8) 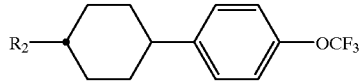
(2-9) 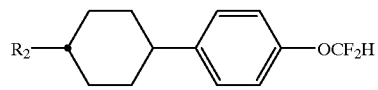
(2-10) 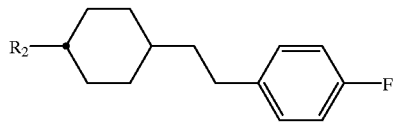
(2-11) 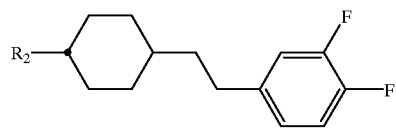
(2-12) 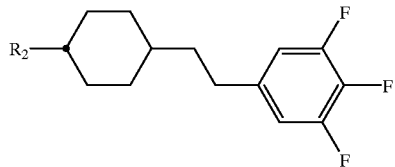
(2-13) 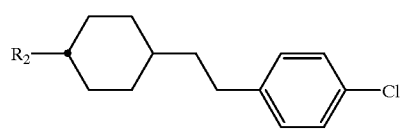
(2-14) 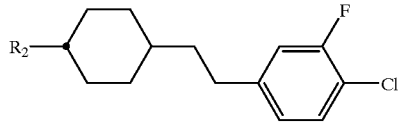
(2-15) 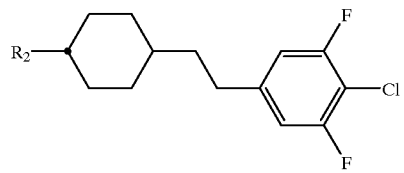
(3-1) 
(3-2) 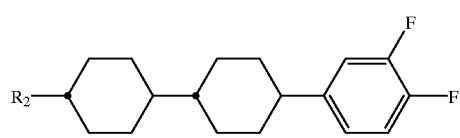
(3-3) 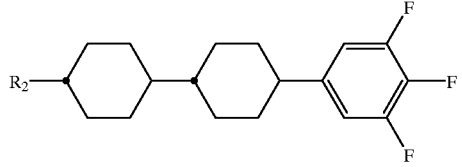

-continued
(3-4)
(3-5)
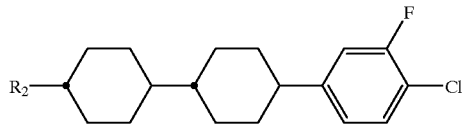
(3-6)
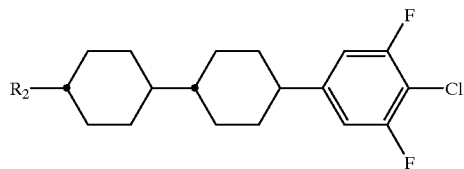
(3-7)
(3-8)
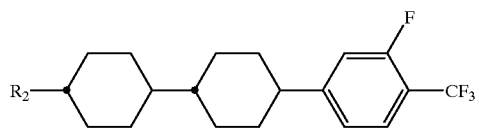
(3-9)
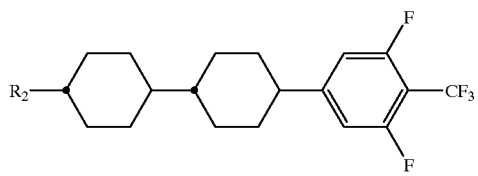
(3-10)
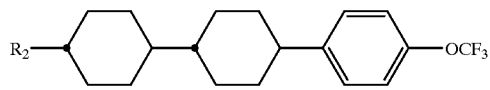
(3-11)
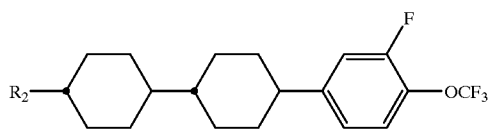
(3-12)
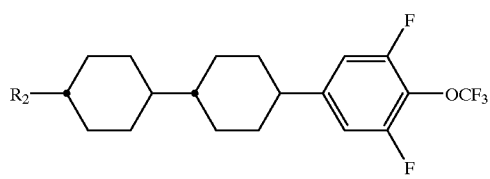
(3-13)
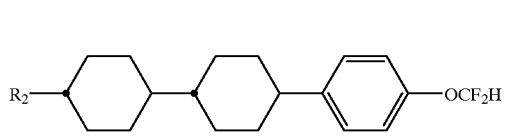
(3-14)
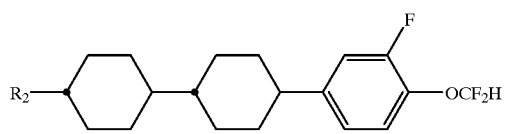
(3-15)
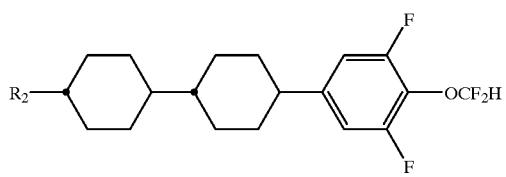
(3-16)
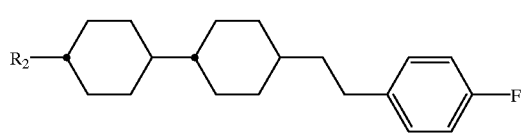
(3-17)
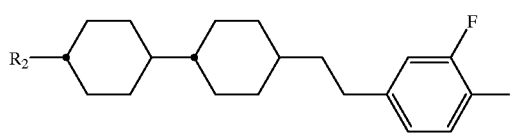
(3-18)
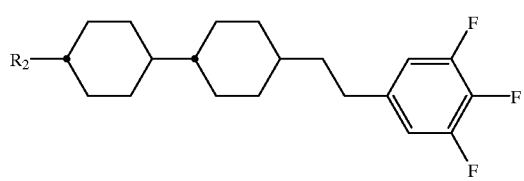
(3-19)
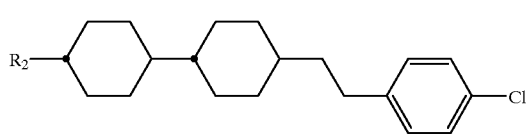

-continued
(3-20) 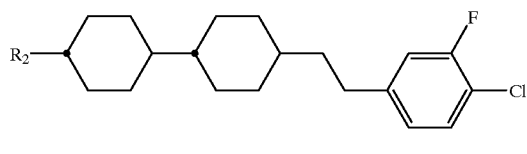
(3-21) 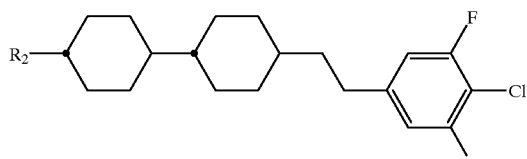
(3-22) 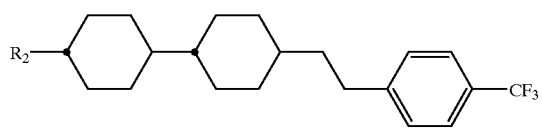
(3-23) 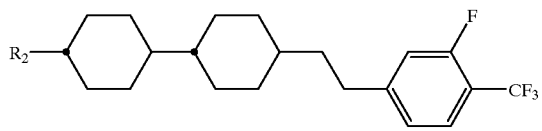
(3-24) 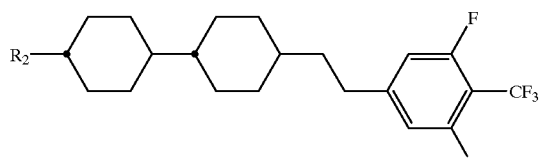
(3-25) 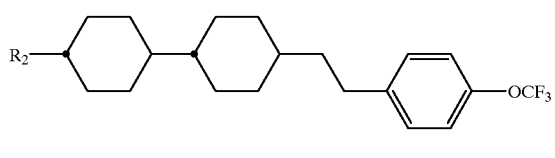
(3-26) 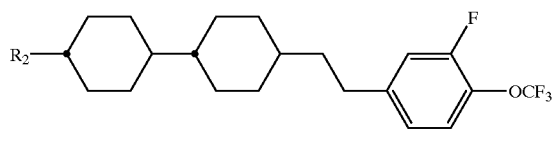
(3-27) 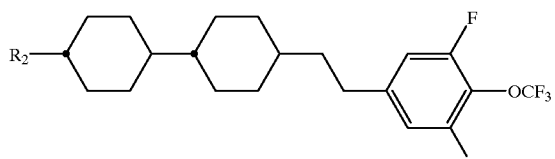
(3-28) 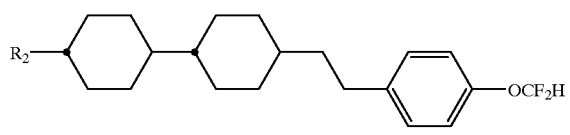
(3-29) 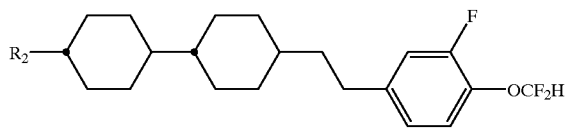
(3-30) 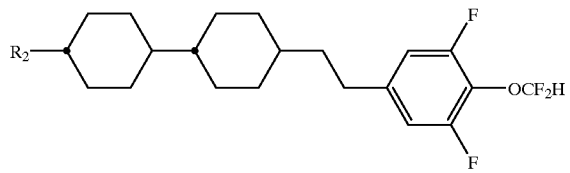
(3-31) 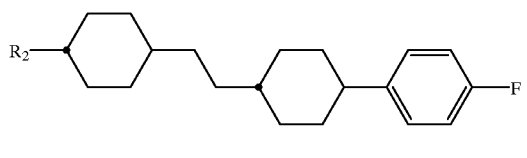
(3-32) 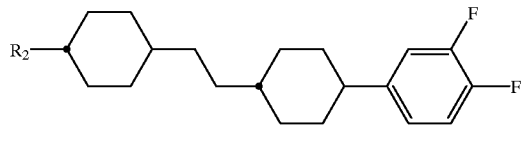
(3-33) 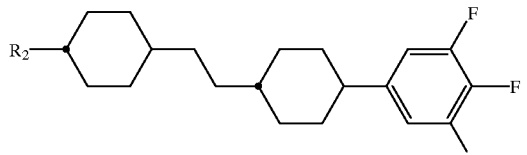
(3-34) 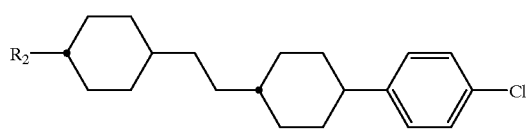
(3-35) 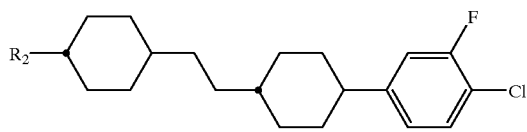

-continued
(3-36)
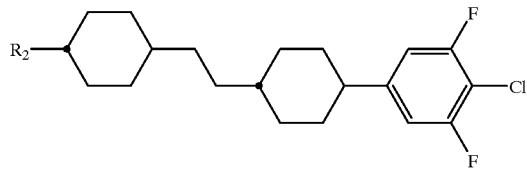
(3-37)
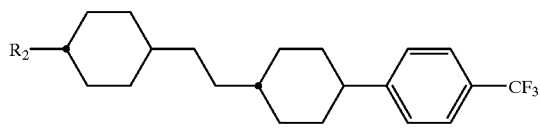
(3-38)
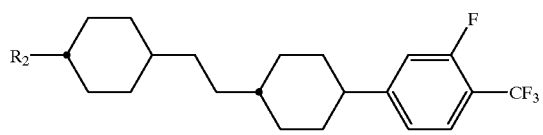
(3-39)
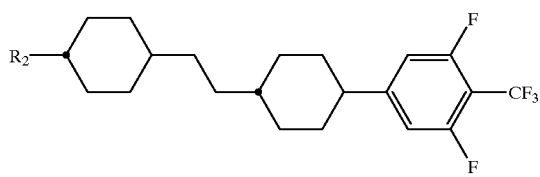
(3-40)
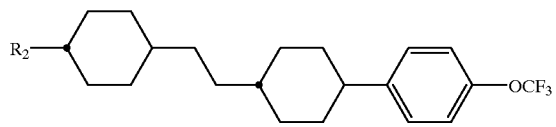
(3-41)
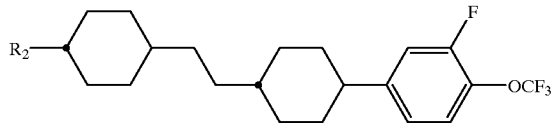
(3-42)
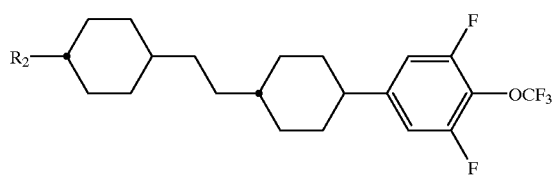
(3-43)
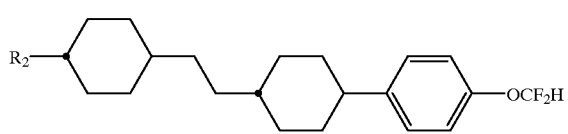
(3-44)
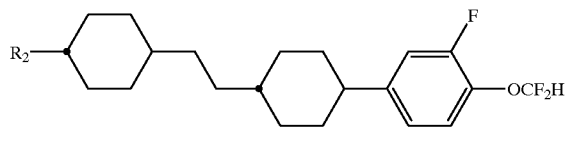
(3-45)
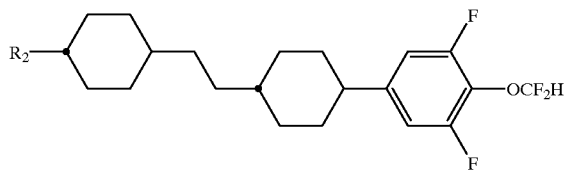
(3-46)
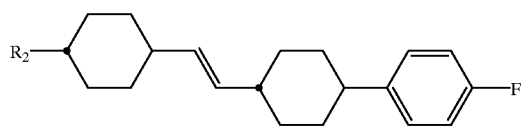
(3-47)
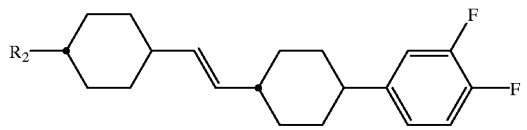
(3-48)
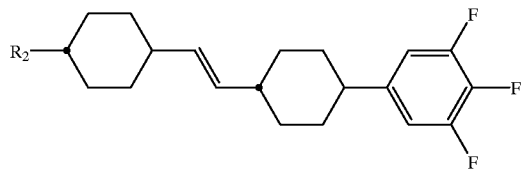
(4-1)
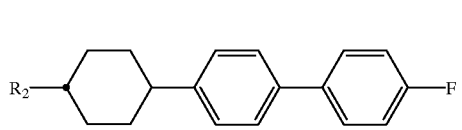
(4-2)
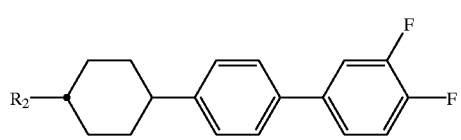
(4-3)
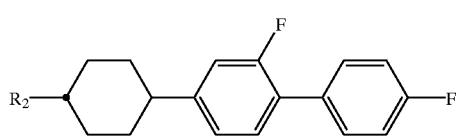

-continued
(4-4)
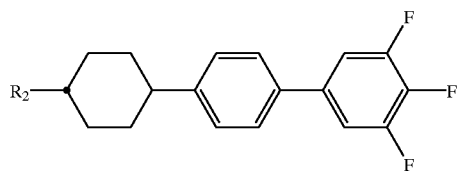
(4-5)
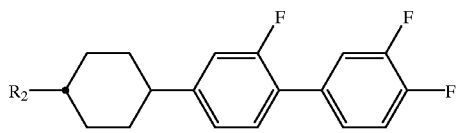
(4-6)
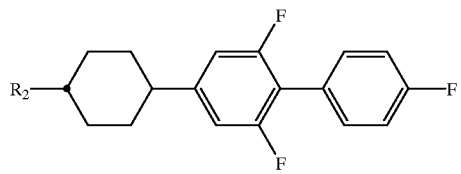
(4-7)
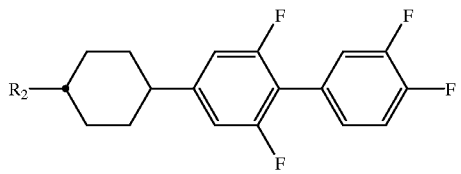
(4-8)
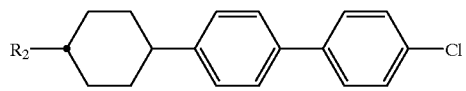
(4-9)
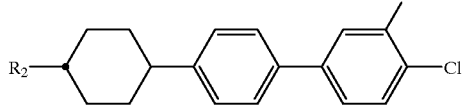
(4-10)
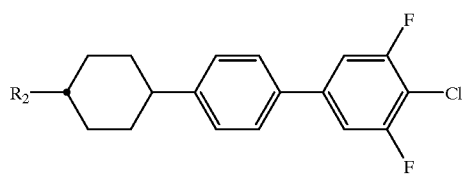
(4-11)
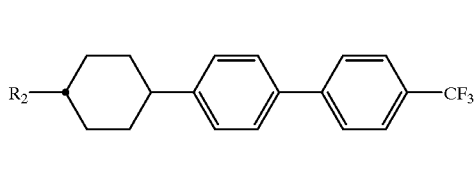
(4-12)
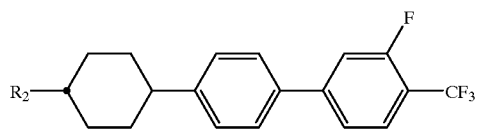
(4-13)
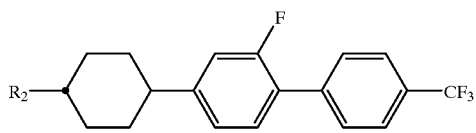
(4-14)
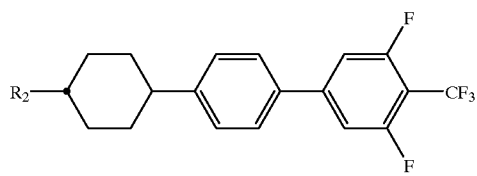
(4-15)
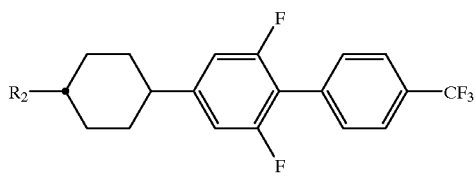
(4-16)
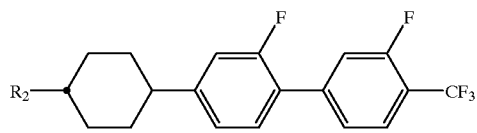
(4-17)
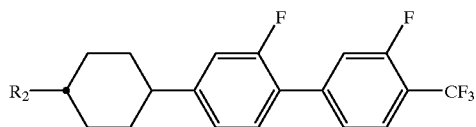
(4-18)
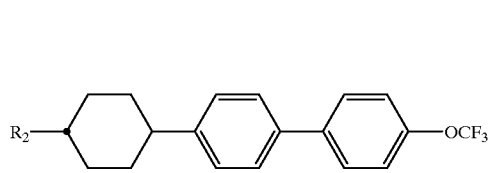
(4-19)
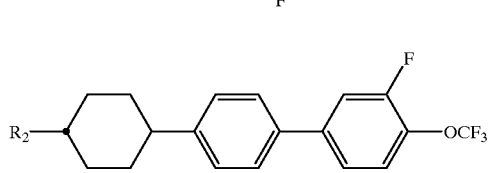
(4-20)
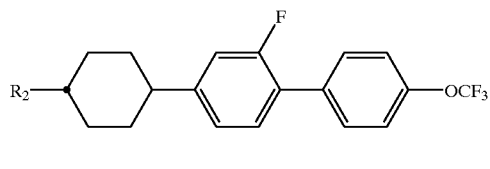
(4-21)
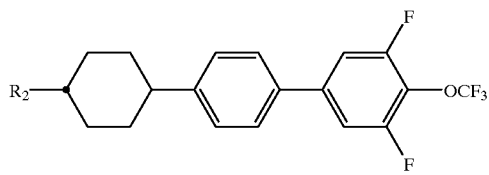

-continued
(4-22)
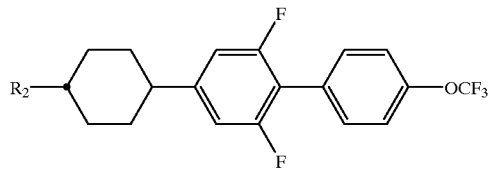
(4-23)
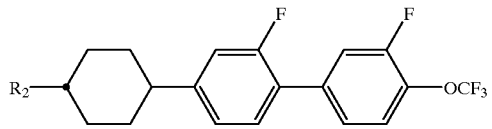
(4-24)
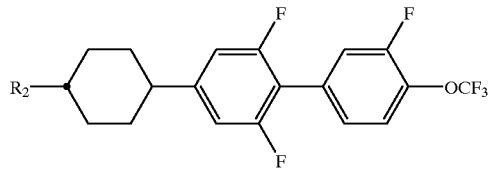
(4-25)
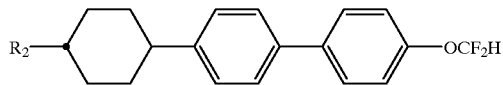
(4-26)
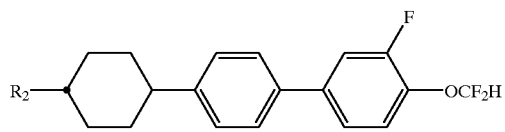
(4-27)
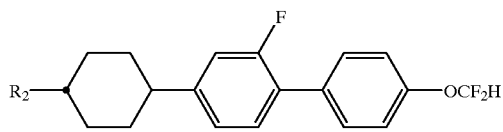
(4-28)
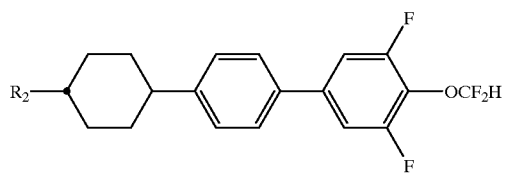
(4-29)
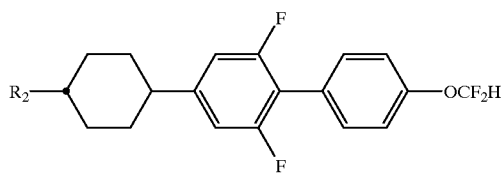
(4-30)
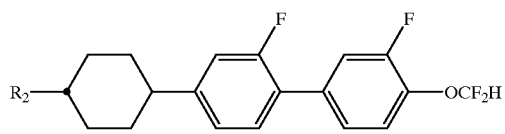
(4-31)
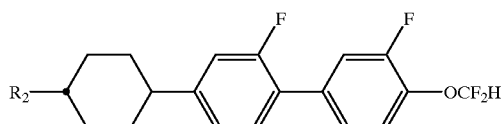
(4-32)
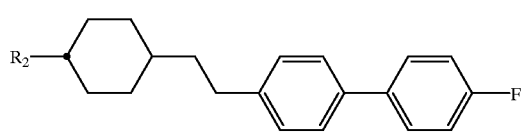
(4-33)
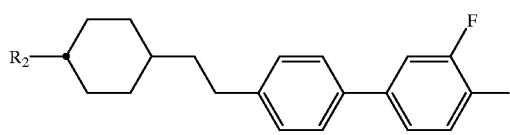
(4-34)
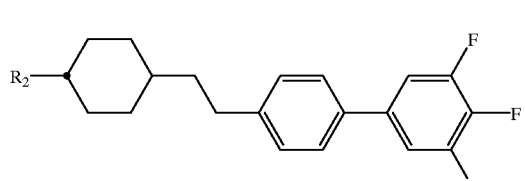
(4-35)
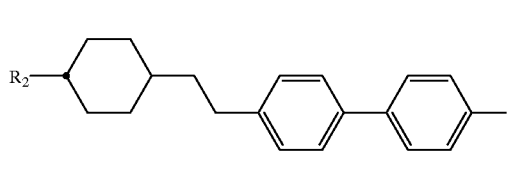
(4-36)
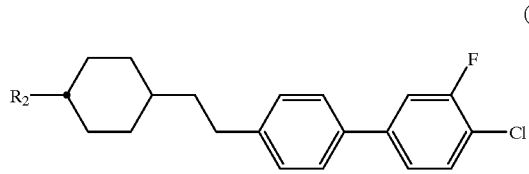
(4-37)
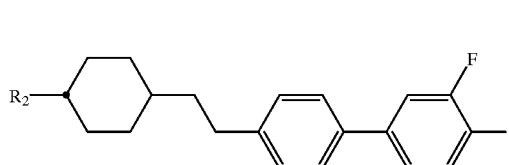

-continued
(4-38)
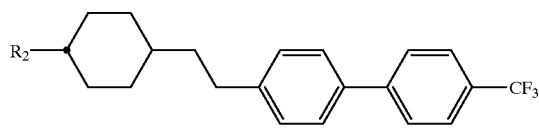
(4-39)
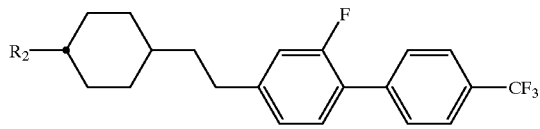
(4-40)
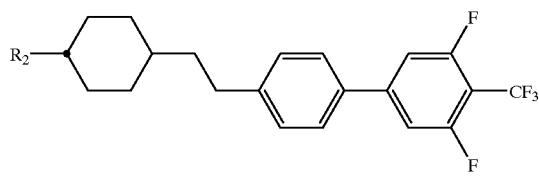
(4-41)
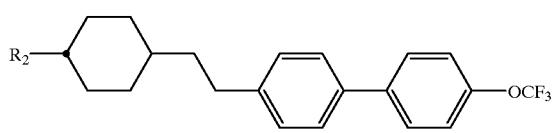
(4-42)
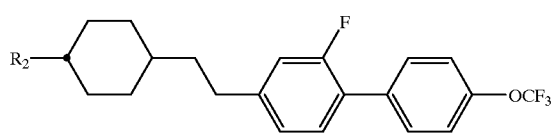
(4-43)
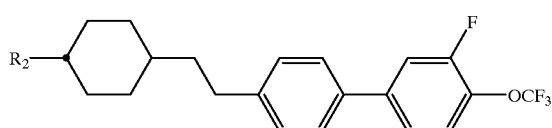
(4-44)
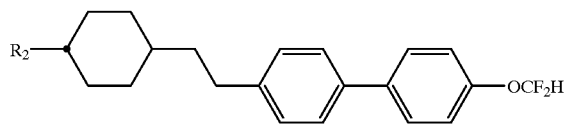
(4-45)
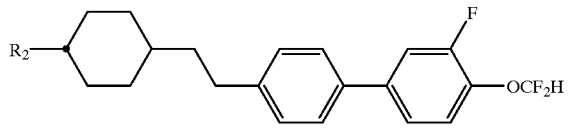
(4-46)
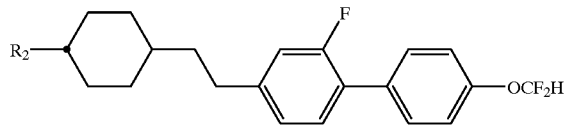
(4-48)
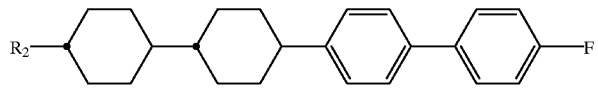
(4-49)
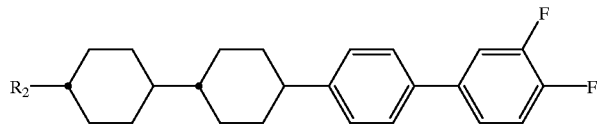
(4-50)
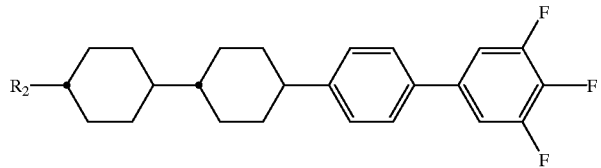
(4-51)
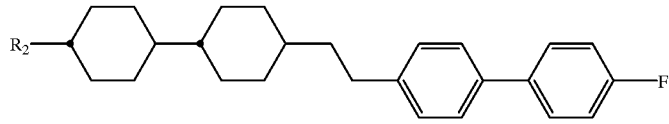

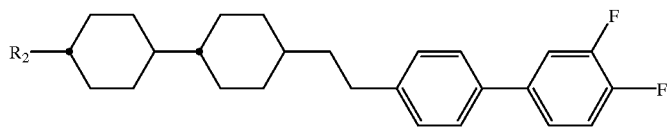

(4-52)

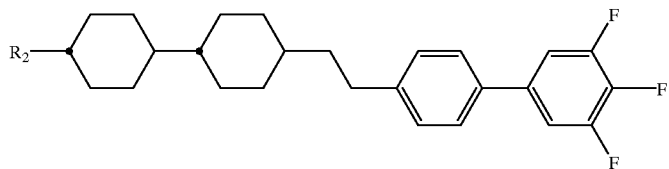

(4-53)

in each of the formulas, $R_2$ has the same meaning as mentioned above.

Compounds expressed by any one of general formulas (2) to (4) have a positive $\Delta\epsilon$ and are remarkably excellent in heat resistance and chemical resistance. Thus, while the compounds are indispensable when the liquid crystal compositions for TFT to which a high reliability particularly such as a high voltage holding ratio (VHR) or a large specific resistance is required are produced, the compounds can be used even when liquid crystal compositions for STN display mode or ordinary TN display mode are produced.

Amount of the compounds to be used is suitably in the range of 1 to 99% by weight, preferably 10 to 97% by weight, and more desirably 40 to 95% by weight based on the total weight of liquid crystal composition when the liquid crystal compositions for TFT are produced.

Among the second B component mentioned above, compounds expressed by any one of formulas (5-1) to (5-24), (6-1) to (6-3), and (7-1) to (7-17) can be mentioned as examples of preferable compounds included in the compounds expressed by general formula (5), (6) or (7).

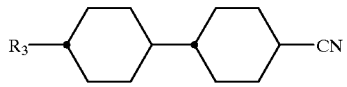
(5-1)

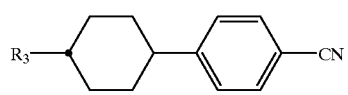
(5-2)

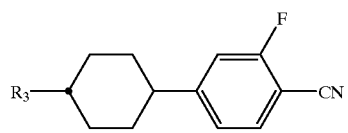
(5-3)

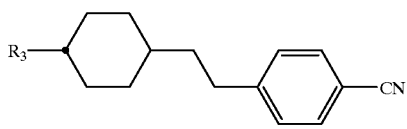
(5-4)

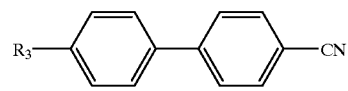
(5-5)

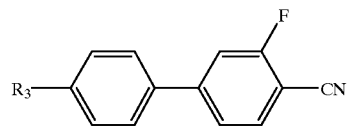
(5-6)

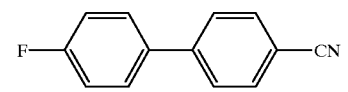
(5-7)

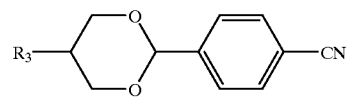
(5-8)

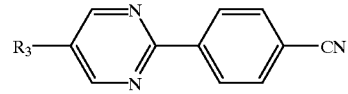
(5-9)

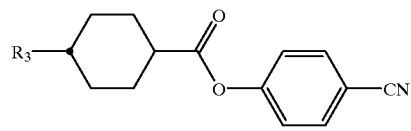
(5-10)

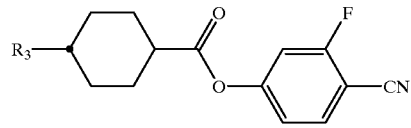
(5-11)

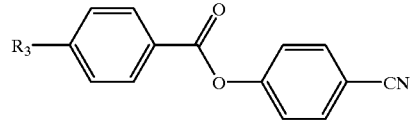
(5-12)

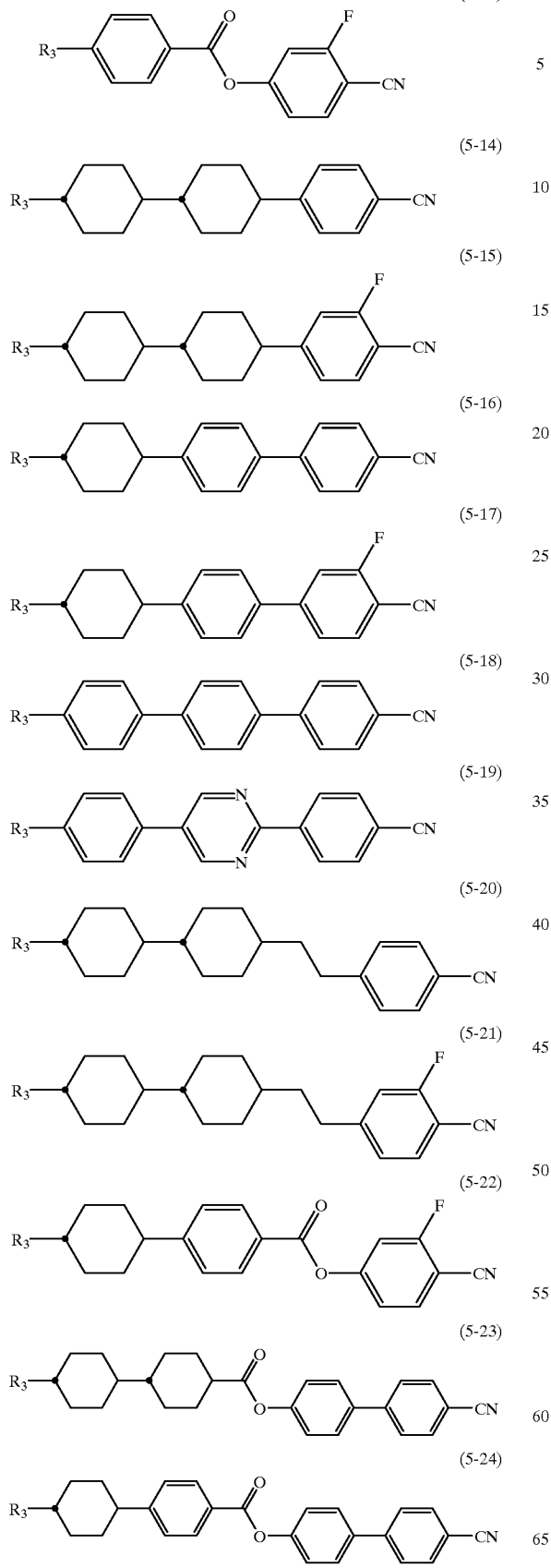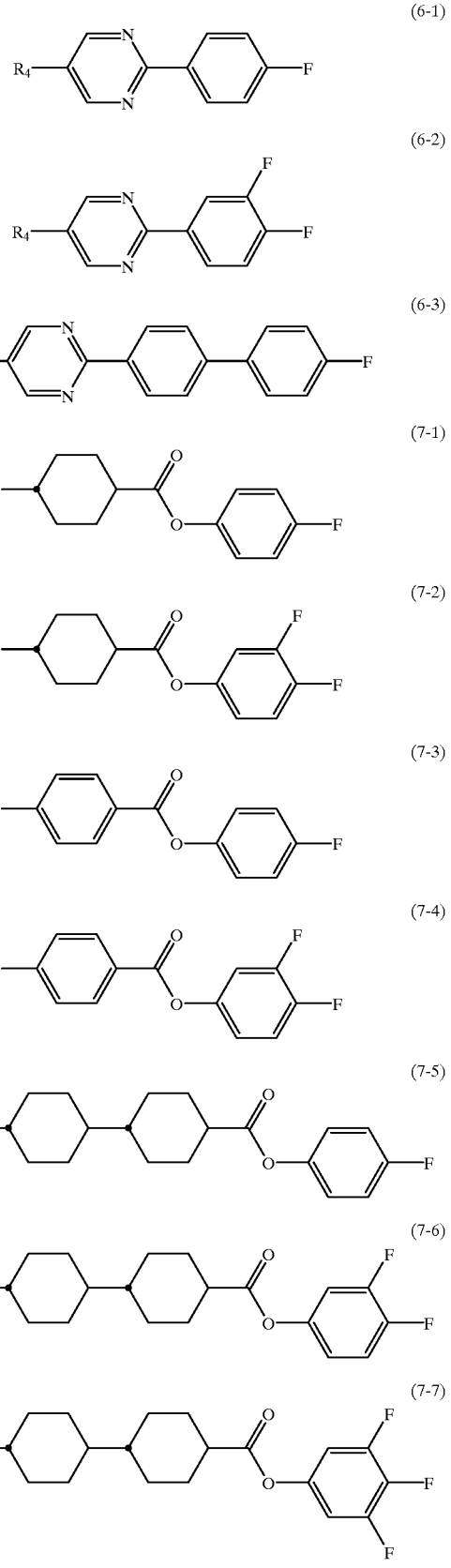

-continued

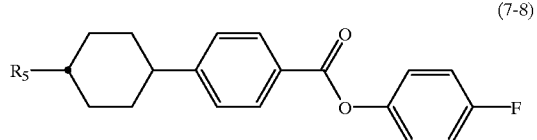
(7-8)

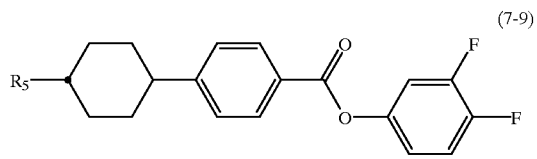
(7-9)

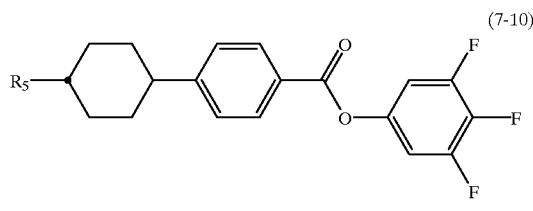
(7-10)

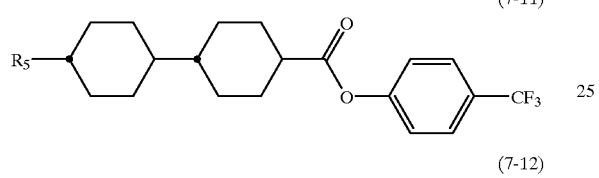
(7-11)

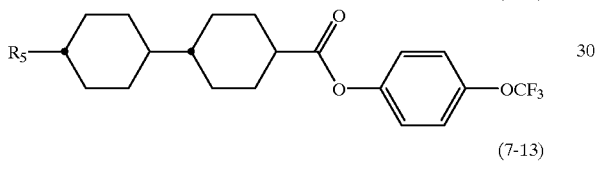
(7-12)

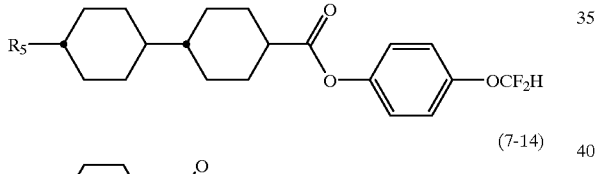
(7-13)

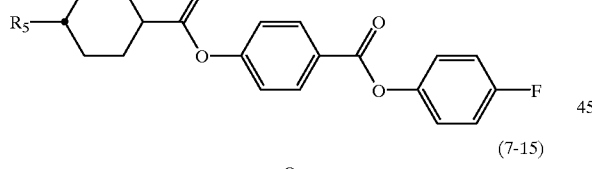
(7-14)

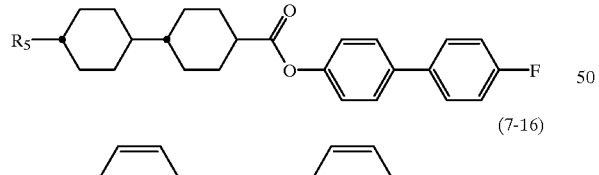
(7-15)

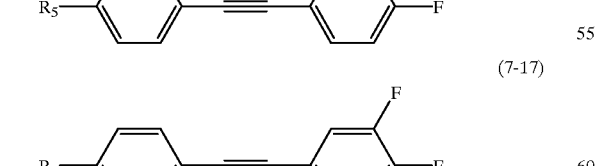
(7-16)

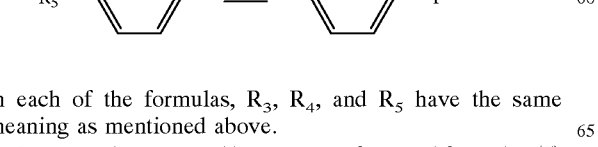
(7-17)

in each of the formulas, $R_3$, $R_4$, and $R_5$ have the same meaning as mentioned above.

Compounds expressed by any one of general formulas (5) to (7) have a large positive $\Delta\epsilon$ and thus are used as component of liquid crystal compositions for the purpose of reducing $V_{th}$. The compounds are also used for adjusting viscosity and $\Delta n$, raising clearing point, widening nematic range, and improving the steepness of $V_{th}$.

Among the second B component, compounds expressed by any one of formulas (8-1) to (8-8) and (9-1) to (9-12) can be mentioned as examples of preferable compounds included in the compounds expressed by general formulas (8) or (9).

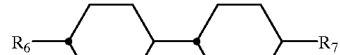
(8-1)

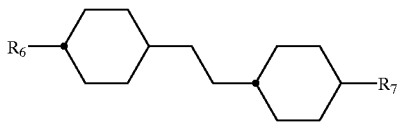
(8-2)

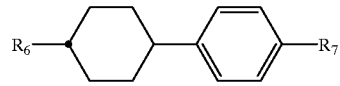
(8-3)

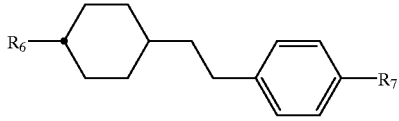
(8-4)

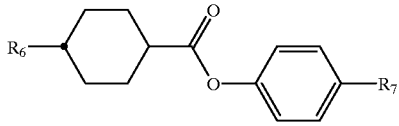
(8-5)

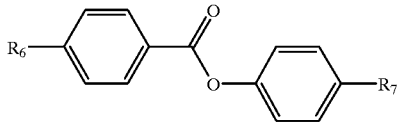
(8-6)

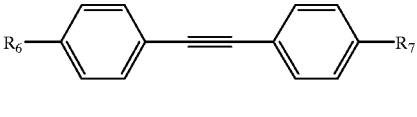
(8-7)

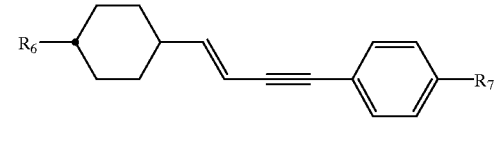
(8-8)

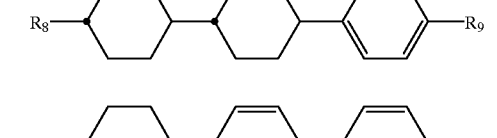
(9-1)

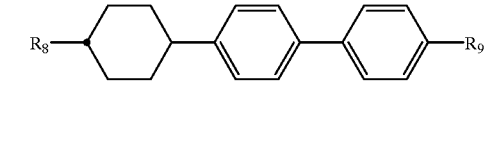
(9-2)

(9-3)
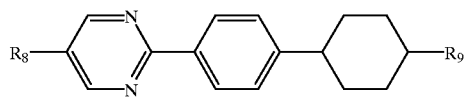

(9-4)
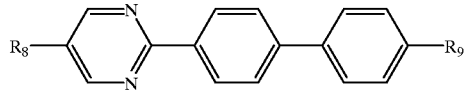

(9-5)
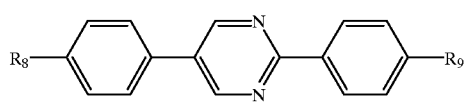

(9-6)
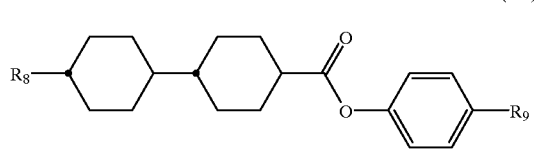

(9-7)
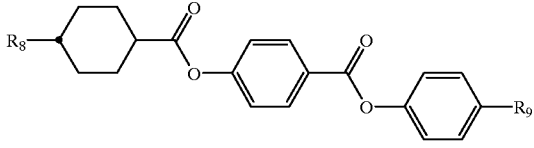

(9-8)
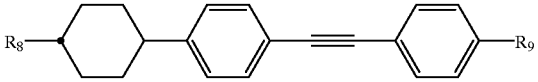

(9-9)
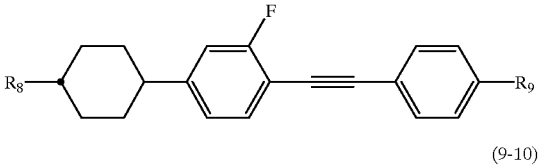

(9-10)
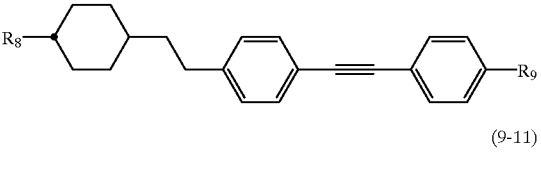

(9-11)
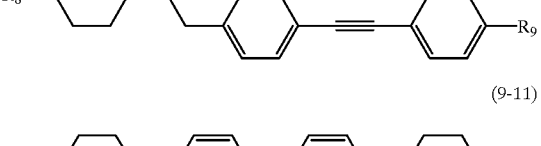

(9-11)
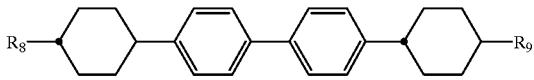

(9-12)
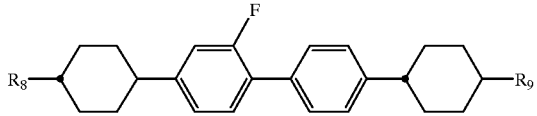

wherein $R_6$, $R_7$, $R_8$, and $R_9$ have the same meaning as mentioned above.

Compounds expressed by general formula (8) or (9) exhibit a negative or small positive $\Delta\epsilon$. Among them, the compounds expressed by general formula (8) are used mainly for the purpose of reducing viscosity and adjusting $\Delta n$, and the compounds expressed by general formula (9) are used mainly for the purpose of raising clearing point, and the purpose of widening nematic range and/or adjusting $\Delta n$.

While the compounds expressed by any one of general formulas (5) to (9) are indispensable particularly when the liquid crystal compositions for STN display mode or ordinary TN display mode are produced, the compounds can be used even when the liquid crystal compositions for TFT are produced.

Amount of the compounds to be used is suitably in the range of 1 to 99% by weight, preferably 10 to 97% by weight, and more desirably in the range of 40 to 95% by weight based on the total weight of liquid crystal composition when the liquid crystal compositions for ordinary TN display mode or STN display mode are produced.

The steepness of $V_{th}$ and viewing angle can be improved by using the liquid crystal compositions of the present invention produced by such methods mentioned above for TFT liquid crystal composition display devices. Also, the response speed of liquid crystal display device can be improved by using the compounds of the present invention expressed by general formula (1) since the compounds have a low viscosity.

Liquid crystal compositions of the present invention preferably contain at least one liquid crystalline compounds expressed by general formula (1) in an amount of 0.1 to 99% by weight to develop excellent characteristics.

Liquid crystal compositions of the present invention are generally produced by conventional methods, for instance, by a method in which each component is mixed to dissolve each other at a high temperature, or each component is dissolved in an organic solvent to mix and then the solvent is distilled off under a reduced pressure.

Also, the liquid crystal compositions of the present invention are improved and optimized in accordance with intended use by adding a suitable additive. Such additives are well known in the art and described in literatures in detail. Usually, a chiral dopant or likes which have an effect of causing a helical structure of liquid crystal to adjust a required twisting angle, and avoiding reverse twist are added.

Further, the liquid crystal compositions of the present invention can be used as ones for guest-host (GH) mode when a dichroic dye such as merocyanine type, styryl type, azo type, azomethine type, azoxy type, quinophthalone type, anthraquinone type, and tetrazine type was added.

Liquid crystal compositions of the present invention can be used even as ones for polymer dispersion type liquid crystal display devices (PDLCD) typified by NCAP which is prepared by forming a nematic liquid crystal into a microcapsule or typified by a polymer network liquid crystal display device (PNLCD) which is prepared by forming a polymer of three-dimensional network structure in a liquid crystal; for electrically controlled birefringence (ECB) mode; and for dynamic scattering (DS) mode.

—C, —CF3, —OCF3, OCF2H, —w, —Ow, or —EMe (in which w is an integer of 1 or more). The number attached to the compounds of the present invention is the same as that shown in the Examples below.

TABLE 1

| Left side terminal group | Symbol | Bonding group | Symbol | Ring structure | Symbol | Right side terminal group | Symbol |
|---|---|---|---|---|---|---|---|
| $C_rH_{2r+1}$— | r— | —$CH_2CH_2$— | 2 |  | B | —F | —F |
| $C_rH_{2r+1}O$— | rO— | —COO— | E | 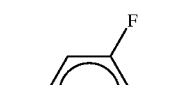 | B(F) | —Cl | —CL |
| $C_rH_{2r+1}OC_sH_{2s}$— | rOs— | —C≡C— | T | 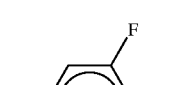 | B(F,F) | —CN | —C |
| $CH_2=CHC_rH_{2r}$— | Vr— | —CH=CH— | V |  | H | —$CF_3$ | —CF3 |
| $C_rH_{2r+1}CH=CHC_sH_{2s}$— | rVs— | —$CF_2O$— | CF2O |  | Py | —$OCF_3$ | —OCF3 |
| $C_rH_{2r+1}CH=CHC_sH_{2s}CH=CHC_kH_{2k}$— | rVsVk— | | | 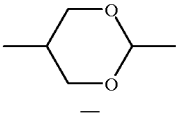 | D | —$OCF_2H$ | —OCF2H |
| | | | |  | Ch | —$C_wH_{2w+1}$ | —w |
| | | | | | | —$OC_wH_{2w+1}$ | —Ow |
| | | | | | | —$COOCH_3$ | —EMe |

While the liquid crystal compositions of the present invention are produced by the methods mentioned above, the following compositions 1 to 21 can be mentioned as examples of the compositions:

In the following composition examples, compounds are designated according to the understanding shown in Table 1. That is, left side terminal group is expressed by r-, rO-, rOs-, Vr-, rvs-, or rVsVk- (in which r, s, and k are an integer of 1 or more); bonding group is expressed by 2, E, T, V, or CF2O; ring structure is expressed by B, B(F), B(F,F), H, Py, D, or Ch; and right side terminal group is expressed by —F, —CL,

| Composition Example 1 | | |
|---|---|---|
| 3-H2B(F)—CF3 | (No. 1) | 5.0% |
| 5-H2B(F)—CF3 | (No. 3) | 5.0% |
| 7-HB(F)—F | | 4.0% |
| 2-HHB(F)—F | | 13.4% |
| 3-HHB(F)—F | | 13.3% |
| 5-HHB(F)—F | | 13.3% |
| 2-H2HB(F)—F | | 6.4% |
| 3-H2HB(F)—F | | 3.2% |
| 5-H2HB(F)—F | | 6.4% |

Composition Example 1

| | | |
|---|---|---|
| 2-HBB(F)—F | | 7.5% |
| 3-HBB(F)—F | | 7.5% |
| 5-HBB(F)—F | | 15.0% |

Composition Example 2

| | | |
|---|---|---|
| 3-H2H2B(F)—OCF3 | (No. 24) | 10.0% |
| 3-H2H2B(F,F)—CF3 | (No. 29) | 10.0% |
| 3-H2H2B(F,F)—OCF3 | (No. 34) | 10.0% |
| 5-H2HB(F,F)—F | | 3.0% |
| 3-HHB(F,F)—F | | 10.0% |
| 4-HHB(F,F)—F | | 6.0% |
| 3-HH2B(F,F)—F | | 3.0% |
| 5-HH2B(F,F)—F | | 3.0% |
| 3-HBB(F,F)—F | | 12.0% |
| 5-HBB(F,F)—F | | 12.0% |
| 3-H2BB(F,F)—F | | 4.0% |
| 3-HBEB(F,F)—F | | 3.0% |
| 3-HHEB(F,F)—F | | 6.0% |
| 4-HHEB(F,F)—F | | 2.0% |
| 5-HHEB(F,F)—F | | 2.0% |
| 3-HHHB(F,F)—F | | 2.0% |
| 3-HH2BB(F,F)—F | | 2.0% |

Composition Example 3

| | | |
|---|---|---|
| 3-HB(F)2B(F)—OCF3 | (No. 60) | 5.0% |
| 3-HB(F)2B(F,F)—OCF3 | (No. 70) | 5.0% |
| 7-HB(F,F)—F | | 4.0% |
| 7-HB(F)—F | | 7.0% |
| 2-HHB(F)—F | | 13.4% |
| 3-HHB(F)—F | | 13.3% |
| 5-HHB(F)—F | | 13.3% |
| 2-H2HB(F)—F | | 4.0% |
| 3-H2HB(F)—F | | 2.0% |
| 5-H2HB(F)—F | | 4.0% |
| 3-H2HB(F,F)—F | | 3.0% |
| 5-H2HB(F,F)—F | | 3.0% |
| 3-HHB(F,F)—F | | 8.0% |
| 3-HH2B(F,F)—F | | 8.0% |
| 5-HH2B(F,F)—F | | 7.0% |

Composition Example 4

| | | |
|---|---|---|
| 3-H2BB(F)—CF3 | (No. 39) | 6.0% |
| 3-H2BB(F)—OCF3 | (No. 44) | 5.0% |
| 3-HB(F)2B(F,F)—OCF3 | (No. 70) | 11.0% |
| 3-HB—CL | | 7.0% |
| 7-HB(F,F)—F | | 10.0% |
| 2-HBB(F)—F | | 5.0% |
| 3-HBB(F)—F | | 5.0% |
| 5-HBB(F)—F | | 10.0% |
| 2-HHB—CL | | 5.0% |
| 4-HHB—CL | | 10.0% |
| 5-HHB—CL | | 5.0% |
| 5-HBB(F,F)—F | | 11.0% |
| 3-HB(F)VB-2 | | 5.0% |
| 3-HB(F)VB-3 | | 5.0% |

Composition Example 5

| | | |
|---|---|---|
| 5-H2B(F)—CF3 | (No. 3) | 5.0% |
| 3-H4B(F)—CF3 | (No. 13) | 5.0% |
| 3-HB(F)2B(F)—OCF3 | (No. 60) | 11.0% |
| 3-H2H2B(F)—OCF3 | (No. 24) | 5.0% |
| 7-HB(F)—F | | 5.0% |
| 7-HB(F,F)—F | | 3.0% |
| 5-H2B(F)—F | | 3.0% |
| 2-HHB(F)—F | | 3.0% |
| 3-HHB(F)—F | | 3.0% |
| 5-HHB(F)—F | | 3.0% |
| 2-HBB(F)—F | | 7.0% |
| 3-HBB(F)—F | | 7.0% |
| 5-HBB(F)—F | | 14.0% |
| 3-HHB—F | | 2.0% |
| 2-HBB—F | | 3.0% |
| 3-HBB—F | | 3.0% |
| 3-HB(F)TB-2 | | 6.0% |
| 3-HB(F)TB-3 | | 6.0% |
| 3-HB(F)TB-4 | | 6.0% |

Composition Example 6

| | | |
|---|---|---|
| 3-H2BB(F)—CF3 | (No. 39) | 8.0% |
| 3-H2H2B(F,F)—CF3 | (No. 29) | 7.0% |
| 5-HEB—F | | 2.5% |
| 7-HEB—F | | 2.5% |
| 2-HHB(F)—F | | 8.0% |
| 3-HHB(F)—F | | 8.0% |
| 5-HHB(F)—F | | 8.0% |
| 2-HBB(F)—F | | 2.5% |
| 3-HBB(F)—F | | 5.0% |
| 5-HBB(F)—F | | 2.5% |
| 4-H2BB(F)—F | | 5.0% |
| 5-H2BB(F)—F | | 6.0% |
| 3-H2HB(F,F)—F | | 10.0% |
| 3-HHB(F,F)—F | | 10.0% |
| 3-HH2B(F,F)—F | | 5.0% |
| 5-HH2B(F,F)—F | | 8.0% |
| 5-HHEBB—F | | 2.0% |

Composition Example 7

| | | |
|---|---|---|
| 3-H2B(F)—CF3 | (No. 1) | 10.0% |
| 3-H2BB(F)—CF3 | (No. 39) | 4.0% |
| V2-HB—C | | 9.0% |
| 1V2-HB—C | | 9.0% |
| 3-HB—C | | 4.0% |
| 1O1-HB—C | | 8.0% |
| 2O1-HB—C | | 4.0% |
| 2-HHB—C | | 3.0% |
| 3-HHB—C | | 3.0% |
| 3-HH-4 | | 10.0% |
| 1O1-HH-5 | | 8.0% |
| 2-BTB—O1 | | 11.0% |
| 3-HHB-1 | | 8.0% |
| 3-HHB-3 | | 9.0% |

Physical parameters of this composition were as follows:

N-I point: 62.8° C.

Viscosity (20° C.): 18.3 mPa·s

Δn (25° C.): 0.112

Δε (25° C.): 7.4

$V_{th}$ (20° C.): 1.68 V

Composition Example 8

| | | |
|---|---|---|
| 3-HB(F)2B(F)—OCF3 | (No. 60) | 3.0% |
| 3-H2H2B(F,F)—OCF3 | (No. 34) | 3.0% |
| V2-HB—C | | 12.0% |
| 1V2-HB—C | | 11.0% |
| 1V2-BEB(F,F)—C | | 5.0% |

Composition Example 8

| | |
|---|---|
| 2-BTB-1 | 8.0% |
| 4-BTB—O2 | 8.0% |
| 5-BTB—O1 | 6.0% |
| 3-HH-4 | 3.0% |
| 3-HH—EMe | 3.0% |
| 3-H2BTB-2 | 4.0% |
| 3-H2BTB-3 | 4.0% |
| 3-H2BTB-4 | 4.0% |
| 2-H2BTB-3 | 4.0% |
| 2-H2BTB-2 | 4.0% |
| 3-HB(F)TB-2 | 6.0% |
| 3-HB(F)TB-3 | 6.0% |
| 3-HB(F)TB-4 | 6.0% |

Composition Example 9

| | | |
|---|---|---|
| 3-H2B(F)—CF3 | (No. 1) | 3.0% |
| 5-H2B(F)—CF3 | (No. 3) | 3.0% |
| 3-H4B(F)—CF3 | (No. 13) | 3.0% |
| 2O1-BEB(F)—C | | 4.0% |
| 3O1-BEB(F)—C | | 3.0% |
| 5O1-BEB(F)—C | | 4.0% |
| 1V2-BEB(F,F)—C | | 15.0% |
| 3-HHEB—F | | 5.0% |
| 5-HHEB—F | | 5.0% |
| 3-HBEB—F | | 6.0% |
| 3-HHB—F | | 3.0% |
| 3-HB—O2 | | 10.0% |
| 3-HH-4 | | 5.0% |
| 3-HHB-1 | | 8.0% |
| 3-HHB-3 | | 6.0% |
| 3-HHB—O1 | | 4.0% |
| 3-H2BTB-2 | | 4.0% |
| 3-H2BTB-3 | | 4.0% |
| 3-HB(F)TB-2 | | 5.0% |

Composition Example 10

| | | |
|---|---|---|
| 3-H2H2B(F)—OCF3 | (No. 24) | 6.0% |
| 3-H2BB(F)—OCF3 | (No. 44) | 3.0% |
| 2-HB(F)—C | | 14.0% |
| 3-HB(F)—C | | 13.0% |
| 5-HB(F)—C | | 9.0% |
| 2-BB—C | | 13.0% |
| 2-BEB—C | | 12.0% |
| 3-BEB—C | | 4.0% |
| 2-HHB(F)—C | | 6.0% |
| 3-HHB(F)—C | | 6.0% |
| 2-HHB—C | | 3.0% |
| 3-HHB—C | | 3.0% |
| 3-PyBB—F | | 8.0% |

Composition Example 11

| | | |
|---|---|---|
| 5-H2B(F)—CF3 | (No. 3) | 3.0% |
| 3-HB(F)2B(F,F)—OCF3 | (No. 60) | 3.0% |
| 2-BB—C | | 8.0% |
| 4-BB—C | | 6.0% |
| 2-HB—C | | 10.0% |
| 3-HB—C | | 10.0% |
| 3-HHB—F | | 4.0% |
| 2-HHB—C | | 3.0% |
| 3-HHB—C | | 3.0% |
| 3-HBEBB—C | | 2.0% |
| 5-PyB—F | | 6.0% |
| 3-PyBB—F | | 6.0% |
| 2-BTB—O1 | | 2.0% |
| 2-HHB-1 | | 6.0% |

Composition Example 11

| | |
|---|---|
| 3-HHB-1 | 8.0% |
| 3-HHB-3 | 15.0% |
| 3-HHB—O1 | 5.0% |

Composition 12

| | | |
|---|---|---|
| 3-H2B(F)—CF3 | (No. 1) | 5.0% |
| 3-DB—C | | 5.0% |
| 4-DB—C | | 12.0% |
| 5-DB—C | | 8.0% |
| 2-BEB—C | | 10.0% |
| 5-PyB(F)—F | | 7.0% |
| 2-PyB-2 | | 1.4% |
| 3-PyB-2 | | 1.3% |
| 4-PyB-2 | | 1.3% |
| 6-PyB—O5 | | 1.5% |
| 6-PyB—O6 | | 1.5% |
| 3-HEB—O4 | | 5.0% |
| 4-HEB—O2 | | 3.7% |
| 3-HEB—O2 | | 3.1% |
| 1O—BEB-2 | | 2.5% |
| 5-HEB-1 | | 3.7% |
| 4-HEB-4 | | 5.0% |
| 3-HHB-3 | | 13.0% |
| 3-HHB—O1 | | 4.0% |
| 2-PyBH-3 | | 4.0% |
| 3-PyBB-2 | | 2.0% |

Composition Example 13

| | | |
|---|---|---|
| 3-H2BB(F)—CF3 | (No. 39) | 6.0% |
| 3-H2H2B(F)—OCF3 | (No. 24) | 7.0% |
| 5-HB—F | | 9.0% |
| 6-HB—F | | 7.0% |
| 7-HB—F | | 7.0% |
| 5-HB-3 | | 5.0% |
| 3-HB—O1 | | 5.0% |
| 2-HHB—OCF3 | | 5.0% |
| 3-HHB—OCF3 | | 5.0% |
| 4-HHB—OCF3 | | 5.0% |
| 5-HHB—OCF3 | | 7.0% |
| 3-HH2B—OCF3 | | 2.0% |
| 5-HH2B—OCF3 | | 3.0% |
| 3-HH2B—F | | 3.0% |
| 5-HH2B—F | | 3.0% |
| 5-HBB(F)—F | | 5.0% |
| 5-HH2B(F)—F | | 9.0% |
| 3-HB(F)BH-3 | | 3.0% |
| 5-HB(F)BH-3 | | 2.0% |
| 5-HB(F)BH-5 | | 2.0% |

Composition Example 14

| | | |
|---|---|---|
| 3-H2H2B(F,F)—CF3 | (No. 29) | 6.0% |
| 3-HB(F)2B(F,F)—OCF3 | (No. 70) | 8.0% |
| 5-HB—F | | 4.0% |
| 7-HB—F | | 7.0% |
| 3-HHB—OCF3 | | 12.0% |
| 5-HHB—OCF3 | | 8.0% |
| 3-H2HB—OCF3 | | 5.0% |
| 5-H2HB—OCF3 | | 5.0% |
| 2-HHB(F)—F | | 6.6% |
| 3-HHB(F)—F | | 6.7% |
| 5-HHB(F)—F | | 6.7% |
| 4-H2HB(F,F)—F | | 5.0% |
| 5-H2HB(F,F)—F | | 5.0% |

-continued

| Composition Example 14 | |
|---|---|
| 3-HH2B(F,F)—F | 8.0% |
| 4-HH2B(F,F)—F | 7.0% |

| Composition Example 15 | | |
|---|---|---|
| 3-H2B(F)—CF3 | (No. 1) | 6.0% |
| 5-H2B(F)—CF3 | (No. 3) | 4.0% |
| 2O1-BEB(F)—C | | 6.0% |
| 3O1-BEB(F)—C | | 5.0% |
| 5O1-BEB(F)—C | | 3.0% |
| V—HB—C | | 10.0% |
| 1V—HB—C | | 10.0% |
| 3-HB—C | | 11.0% |
| 2-HHB—C | | 4.0% |
| 3-HHB—C | | 5.0% |
| 4-HHB—C | | 4.0% |
| 5-HHB—C | | 4.0% |
| 3-HB—O2 | | 7.0% |
| V—HHB-1 | | 7.0% |
| V—HBB-2 | | 4.0% |
| 3-H2BTB-2 | | 4.0% |
| 3-H2BTB-3 | | 3.0% |
| 3-H2BTB-4 | | 3.0% |

| Composition Example 16 | | |
|---|---|---|
| 3-HB(F)2B(F)—OCF3 | (No. 60) | 10.0% |
| 3-H2H2B(F)—OCF3 | (No. 24) | 5.0% |
| 2-HB(F)—C | | 10.0% |
| 3-HB(F)—C | | 10.0% |
| 3-HB—O2 | | 10.0% |
| V—HH-5 | | 5.0% |
| V2-HH-3 | | 5.0% |
| 2-BTB—O1 | | 10.0% |
| V—HHB-1 | | 10.0% |
| V—HBB-2 | | 5.0% |
| 1V2-HBB-2 | | 5.0% |
| 3-HHB—O1 | | 5.0% |
| 3-H2BTB-2 | | 5.0% |
| 3-H2BTB-3 | | 5.0% |

| Composition Example 17 | | |
|---|---|---|
| 3-HB(F)2B(F)—OCF3 | (No. 60) | 3.0% |
| 3-H2H2B(F,F)—CF3 | (No. 29) | 3.0% |
| V2-HB—C | | 12.0% |
| 1V2-HB—C | | 11.0 |
| 1V2-BEB(F,F)—C | | 5.0% |
| 2-BTB-1 | | 8.0% |
| 4-BTB—O2 | | 8.0% |
| 5-BTB—O1 | | 6.0% |
| 3-HH-4 | | 3.0% |
| 3-HH-EMe | | 3.0% |
| 3-H2BTB-2 | | 4.0% |
| 3-H2BTB-3 | | 4.0% |
| 3-H2BTB-4 | | 4.0% |
| 2-H2BTB-2 | | 4.0% |
| 2-H2BTB-3 | | 4.0% |
| 3-HB(F)TB-2 | | 6.0% |
| 3-HB(F)TB-3 | | 6.0% |
| 3-HB(F)VB-4 | | 6.0% |

Physical parameters of this composition were as follows:

N-I point: 91.4° C.

Viscosity (20° C.): 25.0 mPa·s $\Delta n$ (25° C.): 0.198

$\Delta \epsilon$ (25° C.): 7.4

$V_{th}$ (20° C.) 1.68 V

| Composition Example 18 | | |
|---|---|---|
| 3-H2B(F)—CF3 | (No. 1) | 4.0% |
| 5-H2B(F)—CF3 | (No. 3) | 4.0% |
| 2O1-BEB(F)—C | | 4.0% |
| 3O1-BEB(F)—C | | 4.0% |
| 5O1-BEB(F)—C | | 4.0% |
| 1V2-BEB(F,F)—C | | 14.0% |
| 3-HBEB—F | | 6.0% |
| 3-HHEB—F | | 5.0% |
| 5-HHEB—F | | 5.0% |
| 3-HHB—F | | 3.0% |
| 3-HB—O2 | | 10.0% |
| 3-HH-4 | | 6.0% |
| 3-HHB-1 | | 8.0% |
| 3-HHB-3 | | 6.0% |
| 3-HHB—O1 | | 4.0% |
| 3-H2BTB-2 | | 4.0% |
| 3-H2BTB-3 | | 4.0% |
| 3-HB(F)TB-2 | | 5.0% |

Physical parameters of this composition were as follows:

N-I point: 88.0° C.

Viscosity (20° C.): 27.0 mPa·s $\Delta n$ (25° C.): 0.122

$\Delta \epsilon$ (25° C.): 18.1

$V_{th}$ (20° C.): 1.24 V

| Composition Example 19 | | |
|---|---|---|
| 3-H2B(F)—CF3 | (No. 1) | 4.0% |
| 3-HB(F)2B(F,F)—OCF3 | (No. 70) | 2.0% |
| 2-BB—C | | 8.0% |
| 4-BB—C | | 6.0% |
| 2-HB—C | | 10.0% |
| 3-HB—C | | 10.0% |
| 3-HHB—F | | 4.0% |
| 2-HHB—C | | 3.0% |
| 3-HHB—C | | 3.0% |
| 3-HBEBB—C | | 2.0% |
| 5-PyB—F | | 6.0% |
| 3-PyBB—F | | 6.0% |
| 2-BTB—O1 | | 2.0% |
| 2-HHB-1 | | 6.0% |
| 3-HHB-1 | | 8.0% |
| 3-HHB-3 | | 15.0% |
| 3-HHB—O1 | | 5.0% |

Physical parameters of this composition were as follows:

N-I point: 90.9° C.

Viscosity (20° C): 21.9 mPa·s $\Delta n$ (25° C.): 0.140

$\Delta \epsilon$ (25° C.): 9.2

$V_{th}$ (20° C.): 1.79 V

| Composition Example 20 | | |
|---|---|---|
| 3-H2H2B(F)—OCF3 | (No. 24) | 2.0% |
| 3-H2BB(F)—OCF3 | (No. 44) | 4.0% |
| 2-HB(F)—C | | 14.0% |
| 3-HB(F)—C | | 12.0% |
| 5-HB(F)—C | | 10.0% |
| 2-BB—C | | 12.0% |
| 4-BEB—C | | 12.0% |
| 3-BEB—C | | 4.0% |
| 2-HHB(F)—C | | 6.0% |
| 3-HHB(F)—C | | 6.0% |

41

-continued

| Composition Example 20 | |
| --- | --- |
| 2-HHB—C | 2.0% |
| 3-HHB—C | 4.0% |
| 3-PyBB—F | 8.0% |
| 3-HB(F)EB(F)—C | 4.0% |

Physical parameters of this composition were as follows:

N-I point: 56.8° C.

Viscosity (20° C.): 51.6 mPa·s $\Delta n$ (25° C.): 0.143

$\Delta \epsilon$ (25° C.): 18.0

$V_{th}$ (20° C.): 0.91 V

| Composition Example 21 | | |
| --- | --- | --- |
| 3-H2B(F)—CF3 | (No. 1) | 5.0% |
| 3-DB—C | | 5.0% |
| 4-DB—C | | 12.0% |
| 5-DB—C | | 8.0% |
| 2-BEB—C | | 10.0% |
| 5-PyB(F)—F | | 7.0% |
| 2-PyB-2 | | 1.4% |
| 3-PyB-2 | | 1.3% |
| 4-PyB-2 | | 1.3% |
| 6-PyB—O4 | | 2.0% |
| 6-PyB—O5 | | 1.0% |
| 3-HEB—O4 | | 5.0% |
| 4-HEB—O2 | | 3.8% |
| 3-HEB—O2 | | 3.0% |
| 1O—BEB-2 | | 2.4% |
| 5-HEB-1 | | 3.8% |
| 4-HEB-4 | | 5.0% |
| 3-HHB-3 | | 13.0% |
| 3-HHB—O1 | | 4.0% |
| 2-PyBH-3 | | 4.0% |
| 2-PyBB-2 | | 2.0% |

Physical parameters of this composition were as follows:

N-I point: 53.6° C.

Viscosity (20° C.): 29.6 mPa·s $\Delta n$ (25° C.): 0.109

$\Delta \epsilon$ (25° C.): 9.3

$V_{th}$ (20° C.): 1.23 V

Compounds of the present invention expressed by general formula (1) can readily be produced by ordinary technique of organic synthetic chemistry, for instance, by suitably combining the technique described in "Organic Synthesis", "Organic Reactions", and "Jikken Kagaku Kouza (Course of Chemical Experiments)". Synthetic examples of those compounds are shown below in which $R_1$, $Y_1$, $X_3$, and $X_4$ have the same meaning as mentioned above, and q is 1 or 0. The abbreviation shown on the left side below indicates the compounds described on the right side, respectively.

DIBAL: Diisobutylaluminum hydride

PTS: p-Toluenesulfonic acid monohydrate

Pd-C: Palladium-carbon

R-Ni: Raney nickel

LAH: Lithium aluminum hydride

42

FSDF: Fluorosulfonyldifluoro acetic acid methyl ester

DPAE: Ethyl diethylphosphino acetate

Chloranil: Tetrachloro-p-benzoquinone

Preparation of the compounds (compounds expressed by general formula (1) wherein n is 0) of the first group in the present invention:

Those compounds can preferably be produced by such a method as mentioned below:

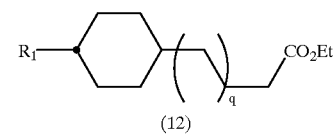

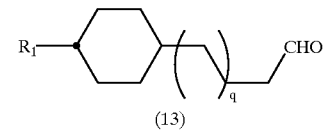

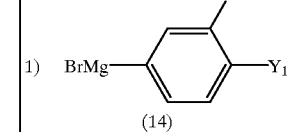

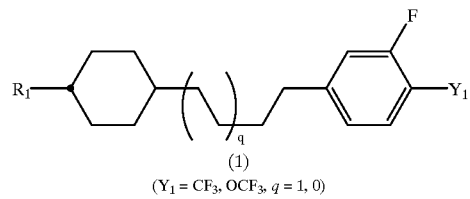

That is, carboxylic acids produced according to a method described in EP 0 315 050 are subjected to an esterification by an ordinary method to obtain ester (12). The ester is reduced with DIBAL to obtain aldehyde (13). The aldehyde is reacted with 3-fluoro-4-substituted phenyl magnesium bromide (14) and then subjected to a dehydration reaction in the presence of an acid catalyst such as PTS and sulfuric acid, and to a hydrogenation reaction using a catalyst such as Pd-C and R-Ni in turn to obtain compounds (1) which are examples of the compounds of the first group in the present invention.

When substituent $Y_1$ in the compounds (1) is trifluoromethyl group in particular, the compounds can be produced even through such a reaction path as follows:

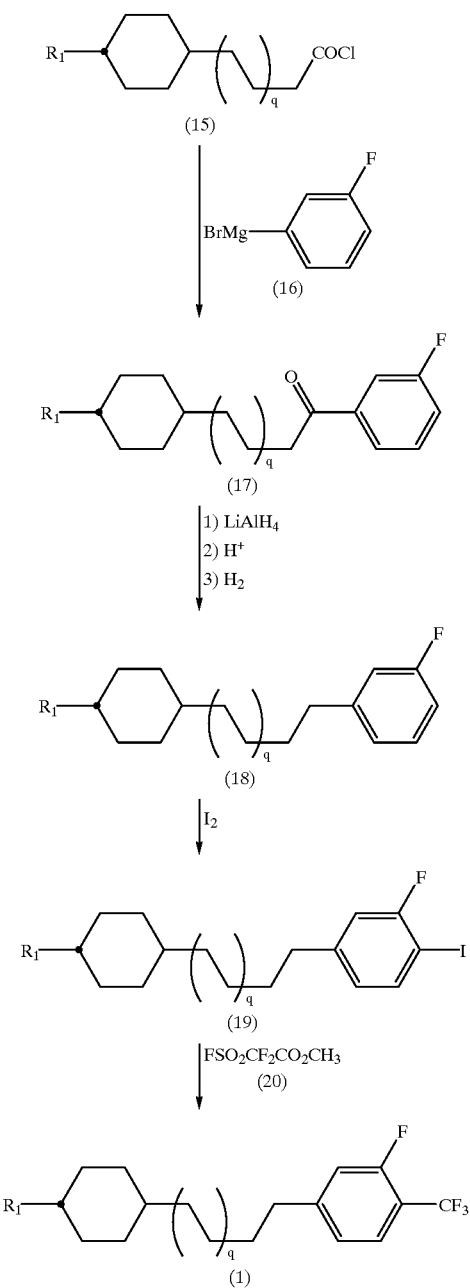

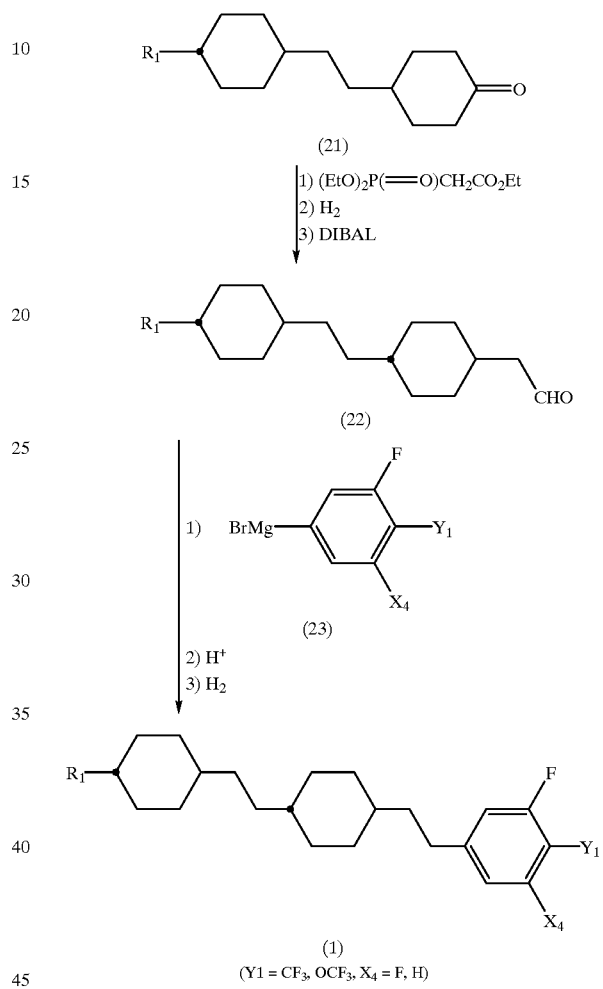

Preparation of the compounds (compounds expressed by general formula (1) wherein n is 1, ring A is 1,4-cyclohexylene, both m and p are 1, and $X_3$ is fluorine atom) of the second group in the present invention:

Those compounds can preferably be prepared by such a method as mentioned below:

That is, carboxylic acids prepared according to a method described in the EP 0 315 050 mentioned above are treated with a method described in Can. J. Chem. 46, 466 (1968) to obtain acid chlorides (15). The acid chlorides are reacted with 3-fluoro-phenyl magnesium bromide (16) according to a method described in Tetrahedron Lett., 25, 4805 (1984) to obtain ketones (17).

The ketones are subjected to a reducing reaction using LAH, to a dehydration reaction under an acidic condition, and to a hydrogenation reaction in turn to obtain compounds (18), and then subjected to an iodination reaction according to a method described in Org. Synth., I, 323 (1941) to obtain iodides (19). The iodides are reacted with FSDS (20) according to a method described in Tetrahedron, 48, 6555 (1992) for trifluoromethylation to obtain the compounds (1) of the first group mentioned above in the present invention in which $Y_1$ is trifluoromethyl group.

That is, cyclohexanone derivatives (21) prepared according to a method described in Chem, Ber., 121, 219 (1988) is reacted with DPAE according to a method described in Org. Synth., V, 547 (1973), and then subjected to a hydrogenation reaction and a reducing reaction with DIBAL in turn to produce aldehydes (22).

The aldehydes are reacted with 3-fluoro-4-substituted phenyl magnesium bromide or 3,4-difluoro-4-substituted phenyl magnesium bromide (23) and then subjected to a dehydration reaction under an acidic condition and to a hydrogenation reaction in the same manner as mentioned above to obtain the compounds (1) of the second group.

Preparation of the compounds (compounds expressed by general formula (1) wherein n is 1, ring A is 1,4-phenylene, m is 1, p is 0, $X_1$, $X_2$ and $X_4$ are hydrogen atom, and $X_3$ is fluorine atom) of the third group in the present invention:

Those compounds can preferably be produced by such a method as mentioned below:

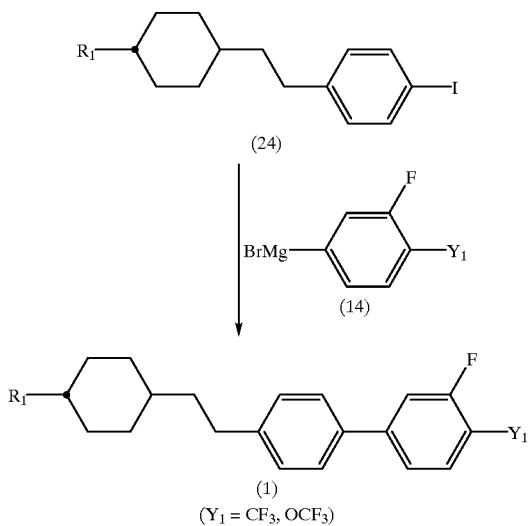

That is, Grignard's reagent (14) is added to iodides (24) prepared according to a method described in WO 9014405 according to a method described, for example, in J. Org. Chem., 42, 1821 (1977) to perform a cross-coupling reaction thereby producing the compounds (1) of the third group in the present invention.

Among the third group compounds (1), the compounds in which $Y_1$ is trifluoromethyl group in particular can be prepared even by such a method as mentioned below:

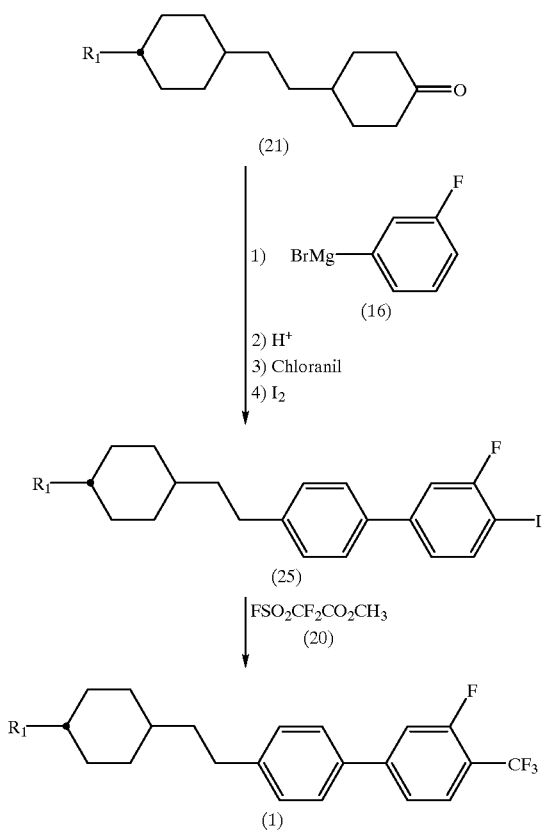

That is, 3-fluorophenyl magnesium bromide is added to the cyclohexanone derivatives (21) mentioned above and then subjected to a dehydration reaction under an acidic condition, to a dehydrogenation using chloranil, and to an iodination reaction in turn to produce iodides (25). Then, the iodides are reacted with FSDS (20) in the same manner as in the case wherein the compounds of the first group are prepared to obtain the compounds (1) of the third group in the present invention.

Preparation of the compounds (compounds expressed by general formula (1) wherein n is 1, ring A is 1,4-phenylene, m is 0, p is 1, $X_1$ is fluorine atom, and $X_2$ is hydrogen atom) of the fourth group in the present invention:

Those compounds can preferably be prepared by such a method as mentioned below:

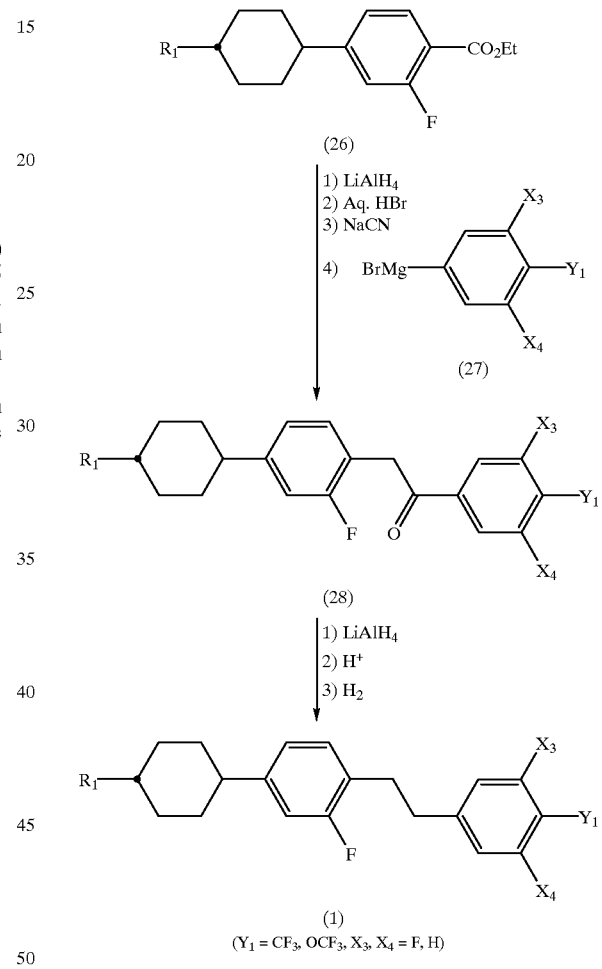

That is, cyano compounds produced according to a method described in Mol. Cryst. Liq. Cryst., 82, 331 (1982) are hydrolyzed and then esterified to obtain compounds (26). The compounds are subjected to the LAH reducing reaction mentioned above, treated with hydrobromic acid by a method described in Org. Synth., I, 25 (1941) to form bromides, subjected to a cyanogenation reaction by a method described in J. Am. Chem. Soc., 93, 195 (1971), and then reacted with Grignard's reagent (27) to obtain ketones (28). The ketones are subjected to a reducing reaction with LAH, dehydration reaction under an acidic condition, and hydrogenation reaction in turn to obtain the compounds (1) of the fourth group in the present invention.

According to the present invention, liquid crystalline compounds can be provided which satisfy required characteristics such as a wide temperature range of nematic phase, lower viscosity, large positive Δε, high chemical stability, high miscibility with other liquid crystalline compounds at low temperatures, small dependency of viscosity and Δε on temperature, extremely high value of specific resistance (high voltage holding ratio), and good UV stability, and are suitable particularly as liquid crystalline compounds for TFT.

Accordingly, when the liquid crystalline compounds of the present invention are used as component of liquid crystal compositions, novel liquid crystal compositions having desired physical properties can be provided by properly selecting six membered rings, substituents and/or bonding groups in the elements forming the molecule in addition to the fact that the liquid crystalline compounds have an excellent solubility in other liquid crystal materials.

EXAMPLE

Now, the present invention is described in more detail with reference to Examples. However, it should be understood that the present invention is by no means restricted by such specific Examples. In each of the Examples, C represents a crystal phase, N a nematic phase, S a smectic phase, and I represents an isotropic liquid phase, respectively, and the unit of phase transition temperature is ° C. in every Example.

Example 1

Production of 1-trifluoromethyl-2-fluoro-4-(2-(4-propylcyclohexyl)ethyl)benzene (Compound expressed by general formula (1) wherein $R_1$ is propyl group, m is 1, n and p are 0, $X_1$, $X_2$ and $X_4$ are hydrogen atom, $X_3$ is fluorine atom, and $Y_1$ is trifluoromethyl group; Compound No. 1):

After a mixture of 4-propylcyclohexyl acetic acid (100 mmol) and thionyl chloride (150 mmol) was heated to reflux for 3 hours, excess thionyl chloride was removed under a reduced pressure with an aspirator to obtain a crude product of acid chloride (100 mmol).

Grignard's reagent prepared from 3-fluorobromobenzene (110 mmol), magnesium (110 mmol), and 100 ml of tetrahydrofuran (hereinafter referred to as THF) was added dropwise to a mixture prepared by adding iron acetylacetone (5 mmol) and 300 ml of dried toluene to the acid chloride (100 mmol) at a temperature lower than −50° C. and stirred for 1 hour at the same temperature. The reaction product thus obtained was added in 200 ml of 6M hydrochloric acid and then extracted with toluene (100 ml×2). Extract was dried with anhydrous magnesium sulfate, the solvent was distilled off, and the residue thus obtained was recrystallized from 50 ml of ethanol to obtain 2-fluoro-4-(1-oxo-2-(4-propylcyclohexyl)ethyl)benzene (75 mmol).

Sodium boron hydride (75 mmol) was added to a mixture of the product (75 mmol) with 200 ml of ethanol while keeping a temperature lower than 10° C. and stirred at room temperature for 3 hours. To the reaction product thus obtained was added 50 ml of 6M hydrochloric acid and 200 ml of water, and then extracted with ethyl acetate (100 ml×4). The solvent was distilled from the extract under a reduced pressure to obtain, as residue, 2-fluoro-4-(1-hydroxy-2-(4-propylcyclohexyl)ethyl)benzene (70 mmol).

Toluene in an amount of 100 ml and 1.5 g of p-toluene-sulfonic acid monohydrate were added to the residue (70 mmol), and heated to reflux for 4 hours while removing the water resulted. After allowed to cool, the reaction product was transferred into a separating funnel, washed with water (100×3), dried with anhydrous magnesium sulfate, and then subjected to a distillation to distill off the solvent under a reduced pressure thereby obtaining a crude 2-fluoro-4-(2-(4-propylcyclo-hexyl)ethenyl)benzene (66 mmol).

Ethanol in an amount of 70 ml, 60 ml of ethyl acetate, and 3 g of 5% palladium carbon as catalyst were added to the crude product (66 mmol) to obtain a mixture. The mixture was stirred under hydrogen gas atmosphere for 4 hours and subjected to a the filtration off of the catalyst and then subjected to the distillation off of the solvent. The residue thus obtained was subjected to a silica gel column chromatography (eluent: heptane) and the purified by recrystallization (ethanol 25 ml ×2) to obtain 2-fluoro-4-(2-(4-propylcyclohexyl)ethyl)benzene (34 mmol).

Iodine (34 mmol), iodic acid (18 mmol), 100 ml of acetic acid, 20 ml of water, and 20 ml of carbon tetrachloride were added to the purified product (34 mmol) to obtain a mixture, and the mixture was heated to reflux for 12 hours. After allowed to cool, 500 ml of water was added to the reaction product and extracted with toluene (200 ml). After the extract was dried with anhydrous magnesium sulfate, the solvent was distilled off under a reduced pressure to obtain a yellow oily product.

Mixture prepared by adding thiourea (264 mmol) and ethanol (600 ml) to the yellow oily product was heated, and the homogeneous solution thus obtained was allowed to stand overnight at room temperature.

Precipitated needle-shaped crystals were filtered off, decomposed with water at 90° C., extracted with 100 ml of heptane, and then dried with anhydrous magnesium sulfate. The solvent was distilled off under a reduced pressure and the residue thus obtained was recrystallized from 20 ml of ethanol to obtain 1-iodo-2-fluoro-4-(2-(4-propylcyclohexyl)ethyl)benzene (10 mmol).

To this product (10 mmol) was added fluorosulfonyldifluoro acetic acid methyl ester (100 mmol), copper iodide (10 mmol), and 20 ml of dimethyl formamide to obtain a mixture, and the mixture was stirred at 90° C. for 2 hours. Water in an amount of 100 ml was added to the reaction product thus obtained, extracted with 100 ml of toluene and then washed with water (50 ml×3). After dried with anhydrous magnesium sulfate, the solvent was distilled off under a reduced pressure, and the residue thus obtained was subjected to a silica gel column chromatography (eluent: heptane) and then purified by conducting a recrystallization (ethanol 10 ml×2) to obtain 5.5 mmol of the subject compound (yield: 55 %).

Various kinds of spectral data well supported its structure. Phase transition temperature of the compound was C - I point: 11.7° C.

According to the method in Example 1, the following compounds (compound Nos. 2 to 18) of the first group were prepared:

| No. | |
|---|---|
| 2 | 1-trifluoromethyl-2-fluoro-4-(2-(4-butylcyclohexyl)ethyl) benzene |
| 3 | 1-trifluoromethyl-2-fluoro-4-(2-(4-penylcyclohexyl)ethyl) benzene<br>C - I point: 21.4° C. |
| 4 | 1-trifluoromethyl-2-fluoro-4-(2-(4-hexylcyclohexyl)ethyl) benzene |
| 5 | 1-trifluoromethyl-2-fluoro-4-(2-(4-heptylcyclohexyl)ethyl) benzene |
| 6 | 1-trifluoromethyl-2-fluoro-4-(2-(4-octylcyclohexyl)ethyl) benzene |

| No. | |
|---|---|
| 7 | 1-trifluoromethyl-2-fluoro-4-(4-(4-propylcyclohexyl)butyl)benzene |
| 8 | 1-trifluoromethyl-2-fluoro-4-(4-(4-butylcyclohexyl)butyl)benzene |
| 9 | 1-trifluoromethyl-2-fluoro-4-(4-(4-pentylcyclohexyl)butyl)benzene |
| 10 | 1-trifluoromethyl-2-fluoro-4-(4-(4-hexylcyclohexyl)butyl)benzene |
| 11 | 1-trifluoromethyl-2-fluoro-4-(4-(4-heptylcyclohexyl)butyl)benzene |
| 12 | 1-trifluoromethyl-2-fluoro-4-(4-(4-octylcyclohexyl)butyl)benzene |
| 13 | 1-trifluoromethoxy-2-fluoro-4-(2-(4-propylcyclohexyl)ethyl)benzene |
| 14 | 1-trifluoromethoxy-2-fluoro-4-(2-(4-butylcyclohexyl)ethyl)benzene |
| 15 | 1-trifluoromethoxy-2-fluoro-4-(2-(4-pentylcyclohexyl)ethyl)benzene |
| 16 | 1-trifluoromethoxy-2-fluoro-4-(2-(4-hexylcyclohexyl)ethyl)benzene |
| 17 | 1-trifluoromethoxy-2-fluoro-4-(2-(4-heptylcyclohexyl)ethyl)benzene |
| 18 | 1-trifluoromethoxy-2-fluoro-4-(2-(4-octylcyclohexyl)ethyl)benzene |

Example 2

Production of 1-trifluoromethoxy-2-fluoro-4-(2-(4-(2-(4-propylcyclohexyl)ethyl)cyclohexyl)ethyl)benzene (Compound expressed by general formula (1) wherein $R_1$ is propyl group, m, n, and p are 1, ring A is 1,4-cyclohexylene, $X_1$, $X_2$ and $X_4$ are hydrogen atom, $X_3$ is fluorine atom, and $Y_1$ is trifluoromethoxy group; Compound No. 19):

Grignard's reagent prepared from 3-fluoro- 4-trifluoromethoxybromobenzene (55 mmol), magnesium (55 mmol), and 80 ml of THF was added dropwise to a mixture of 4-(2-(4-propylcyclohexyl) ethyl)cyclohexyl-acetaldehyde (50 mmol) which was prepared according to the method mentioned above for preparing aldehydes (22) to be used as a starting material of the compounds (second group) in the present invention and 50 ml of THF at a temperature lower than 0° C. After the reaction product was stirred at room temperature for 3 hours, 200 ml of 6M hydrochloric acid was added thereto and extracted with ethyl acetate (100 ml×2). Extract was dried with anhydrous magnesium sulfate, and then the solvent was distilled off.

Toluene in an amount of 100 ml and 1 g of p-toluenesulfonic acid monohydrate were added to the residue thus obtained, and heated to reflux for 4 hours while removing the water resulted. After allowed to cool, the reaction product was emptied into a separating funnel, washed with water (100 ml×3), dried with anhydrous magnesium sulfate, and subjected to a distillation under a reduced pressure to distill off the solvent thereby obtaining a crude 1-trifluoromethoxy-2-fluoro-4-(2-(4-(2-(4-propylcyclohexyl)ethyl)cyclohexyl)ethenyl)benzene (43 mmol).

To this product (43 mmol) were added 50 ml of ethanol, 50 ml of ethyl acetate, and 2 g of 5% palladium carbon as catalyst to obtain a mixture and the mixture was stirred under hydrogen gas atmosphere for 3 hours. The catalyst was filtered off, the solvent was distilled off, and the residue thus obtained was subjected to a silica gel column chromatography (eluent: heptane) and then purified by a recrystallization (ethanol 10 ml×2) to obtain 16.5 mmol of the subject compound (yield: 33 %).

Various kinds of spectral data well supported its structure. Phase transition temperature of the compound was C - N point: 50.3° C., and N - I point: 101.7° C.

According to the method in Example 2, the following compounds (compound Nos. 20 to 38) of the second group were prepared:

| No. | |
|---|---|
| 20 | 1-trifluoromethyl-2-fluoro-4-(2-(4-(2-(4-propylcyclohexyl)ethyl)cyclohexyl)ethyl)benzene |
| 21 | 1-trifluoromethyl-2-fluoro-4-(2-(4-(2-(4-butylcyclohexyl)ethyl)cyclohexyl)ethyl)benzene |
| 22 | 1-trifluoromethyl-2-fluoro-4-(2-(4-(2-(4-pentylcyclohexyl)ethyl)cyclohexyl)ethyl)benzene |
| 23 | 1-trifluoromethyl-2-fluoro-4-(2-(4-(2-(4-hexylcyclohexyl)ethyl)cyclohexyl)ethyl)benzene |
| 24 | 1-trifluoromethyl-2-fluoro-4-(2-(4-(2-(4-heptylcyclohexyl)ethyl)cyclohexyl)ethyl)benzene |
| 25 | 1-trifluoromethoxy-2-fluoro-4-(2-(4-(2-(4-propylcyclohexyl)ethyl)cyclohexyl)ethyl)benzene<br>C - N point: 50.3° C., N - I point: 101.7° C. |
| 25' | 1-trifluoromethoxy-2-fluoro-4-(2-(4-(2-(4-butylcyclohexyl)ethyl)cyclohexyl)ethyl)benzene |
| 26 | 1-trifluoromethoxy-2-fluoro-4-(2-(4-(2-(4-pentylcyclohexyl)ethyl)cyclohexyl)ethyl)benzene |
| 27 | 1-trifluoromethoxy-2-fluoro-4-(2-(4-(2-(4-hexylcyclohexyl)ethyl)cyclohexyl)ethyl)benzene |
| 28 | 1-trifluoromethoxy-2-fluoro-4-(2-(4-(2-(4-heptylcyclohexyl)ethyl)cyclohexyl)ethyl)benzene |
| 29 | 1-trifluoromethyl-2,6-difluoro-4-(2-(4-(2-(4-propylcyclohexyl)ethyl)cyclohexyl)ethyl)benzene<br>C - N point: 88.9° C., N - I point: 81.9° C. |
| 30 | 1-trifluoromethyl-2,6-difluoro-4-(2-(4-(2-(4-butylcyclohexyl)ethyl)cyclohexyl)ethyl)benzene |
| 31 | 1-trifluoromethyl-2,6-difluoro-4-(2-(4-(2-(4-pentylcyclohexyl)ethyl)cyclohexyl)ethyl)benzene |
| 32 | 1-trifluoromethyl-2,6-difluoro-4-(2-(4-(2-(4-hexylcyclohexyl)ethyl)cyclohexyl)ethyl)benzene |
| 33 | 1-trifluoromethyl-2,6-difluoro-4-(2-(4-(2-(4-heptylcyclohexyl)ethyl)cyclohexyl)ethyl)benzene |
| 34 | 1-trifluoromethyl-2,6-difluoro-4-(2-(4-(2-(4-propylcyclohexyl)ethyl)cyclohexyl)ethyl)benzene |
| 35 | 1-trifluoromethyl-2,6-difluoro-4-(2-(4-(2-(4-butylcyclohexyl)ethyl)cyclohexyl)ethyl)benzene |
| 36 | 1-trifluoromethyl-2,6-difluoro-4-(2-(4-(2-(4-pentylcyclohexyl)ethyl)cyclohexyl)ethyl)benzene |
| 37 | 1-trifluoromethyl-2,6-difluoro-4-(2-(4-(2-(4-hexylcyclohexyl)ethyl)cyclohexyl)ethyl)benzene |
| 38 | 1-trifluoromethyl-2,6-difluoro-4-(2-(4-(2-(4-heptylcyclohexyl)ethyl)cyclohexyl)ethyl)benzene |

Example 3

Production of 4'-(2-(4-propylcycohexyl)ethyl)-3-fluoro-4-trifluoromethoxybiphenyl (Compound expressed by general formula (1) wherein $R_1$ is propyl group, m and n are 1, p is 0, ring A is 1,4-phenylene, $X_1$, $X_2$ and $X_4$ are hydrogen atom, $X_3$ is fluorine atom, and $Y_1$ is trifluoromethoxy group; Compound No. 39):

A mixture containing 1-iodo-4-(2-(4-propylcyclohexyl)ethyl)benzene (50 mmol) prepared as a starting material for the compounds of the third group according to a method described in the WO 9014405 mentioned above, 100 ml of THF, and palladium chloride (1 mmol) was heated to reflux, and Grignard's reagent prepared from 3-fluoro-4-trifluoromethoxybromobenzene (55 mmol), magnesium (55 mmol), and 80 ml of THF was added dropwise thereto in 1 hour and then further refluxed for 1 hour. After allowed to cool, 200 ml of 6M hydrochloric acid was added to the reaction product and then extracted with toluene (100 ml×2). Extract was dried with anhydrous magnesium sulfate and then the solvent was distilled off. The residue thus obtained was subjected to a silica gel column chromatography (eluent: heptane) and then purified by a recrystallization (ethanol 10 ml×2) to obtain 39 mmol of the subject compound (yield: 78 %).

Various kinds of spectral data well supported its structure. Phase transition temperature of the compound was C - N point: 64.9° C., and N - I point: 87.9° C.

According to the method in Example 3, the following compounds (compound Nos. 40 to 48) of the third group were prepared:

| No. | |
|---|---|
| 40 | 4'-(2-(4-propylcyclohexyl)ethyl)-3-fluoro-4-trifluoromethylbiphenyl<br>C - I point: 88.5° C. |
| 41 | 4'-(2-(4-butylcyclohexyl)ethyl)-3-fluoro-4-trifluoromethylbiphenyl |
| 42 | 4'-(2-(4-pentylcyclohexyl)ethyl)-3-fluoro-4-trifluoromethylbiphenyl |
| 43 | 4'-(2-(4-hexylcyclohexyl)ethyl)-3-fluoro-4-trifluoromethylbiphenyl |
| 44 | 4'-(2-(4-heptylcyclohexyl)ethyl)-3-fluoro-4-trifluoromethylbiphenyl |
| 45 | 4'-(2-(4-butylcyclohexyl)ethyl)-3-fluoro-4-trifluoromethoxybiphenyl |
| 46 | 4'-(2-(4-pentylcyclohexyl)ethyl)-3-fluoro-4-trifluoromethoxybiphenyl |
| 47 | 4'-(2-(4-hexylcyclohexyl)ethyl)-3-fluoro-4-trifluoromethoxybiphenyl |
| 48 | 4'-(2-(4-heptylcyclohexyl)ethyl)-3-fluoro-4-trifluoromethoxybiphenyl |

Example 4

Production of 1-trifluoromethoxy-2-fluoro-4-(2-(2-fluoro-4-(4-propylcyclohexyl)phenyl)ethyl)benzene (Compound expressed by general formula (1) wherein $R_1$ is propyl group, m is 0, n and p are 1, ring A is 1,4-phenylene, $X_1$ and $X_3$ are fluorine atom, $X_2$ and $X_4$ are hydrogen atom, and $Y_1$ is trifluoromethoxy group; Compound No. 49):

After a mixture of 2-fluoro-4-(4-propylcyclohexyl)phenyl acetic acid (100 mmol) with thionyl chloride (150 mmol) was heated to reflux for 3 hours, excess thionyl chloride was removed under a reduced pressure with an aspirator to obtain a crude product of acid chloride (100 mmol).

Grignard's reagent prepared from 3-fluoro-4-trifluoromethoxybromobenzene (110 mmol), magnesium (110 mmol), and 100 ml of THF was added dropwise at a temperature lower than −50° C. to a mixture of the product of acid chloride (100 mmol), iron acetylacetone (5 mmol), and 300 ml of dried toluene, and further stirred at the same temperature for 1 hour. The reaction product thus obtained was added to 200 ml of 6M hydrochloric acid and then extracted with toluene (100 ml×2). Extract was dried with anhydrous magnesium sulfate and then the solvent was distilled off. The residue thus obtained was recrystallized from 50 ml of ethanol to obtain 1-trifluoromethoxy-2-fluoro-4-(1-oxo-2-(2-fluoro-4-(4-propylcyclohexyl)phenyl)ethyl)benzene (70 mmol).

Sodium boron hydride (70 mmol) was added to a mixture of the recrystallized product (70 mmol) with 200 ml of ethanol while maintaining a temperature lower than 10° C., and further stirred at room temperature for 3 hours. To the reaction product thus obtained was added 50 ml of 6M hydrochloric acid and 200 ml of water, and then extracted with ethyl acetate (100 ml×4). The solvent was distilled off under a reduced pressure to obtain 1-trifluoromethoxy-2-fluoro-4-(1-hydroxy-2-(2-fluoro-4-( 4-propylcycohexyl) phenyl)ethyl)benzene (65 mmol) as residue.

Toluene in an amount of 100 ml and 1.5 g of p-toluenesulfonic acid monohydrate were added to the residue (65 mmol), and heated to reflux for 4 hours while removing the water resulted. After allowed to cool, the reaction product was emptied into a separating funnel, washed with water (100 ml×3), and then dried with anhydrous magnesium sulfate. The solvent was distilled off under a reduced pressure to obtain a crude 1-trifluoromethoxy-2-fluoro-4-(1-hydroxy-2-(2-fluoro-4-(4-propylcyclohexyl)phenyl)ethenyl)benzene (59 mmol).

A mixture of the crude compound (59 mmol), 70 ml of ethanol, 60 ml of ethyl acetate, and 3 g of 5 % palladium carbon as catalyst was stirred under hydrogen gas atmosphere for 4 hours.

After the catalyst was filtered off, the solvent was distilled off, and the residue thus obtained was subjected to a silica gel chromatography (eluent: heptane), and then purified by a recrystallization (ethanol 25 ml×2) to obtain 28 mmol of the subject compound (yield: 48 %).

Various kinds of spectral data well supported its structure. Phase transition temperature of the compound was C - I point: 43.8° C.

According to the method in Example 4, the following compounds (compound Nos. 50 to 78) of the fourth group were prepared:

| No. | |
|---|---|
| 50 | 1-trifluoromethyl-4-(2-(2-fluoro-4-(4-propylcyclohexyl) phenyl)ethyl)benzene |
| 51 | 1-trifluoromethyl-4-(2-(2-fluoro-4-(4-butylcyclohexyl) phenyl)ethyl)benzene |
| 52 | 1-trifluoromethyl-4-(2-(2-fluoro-4-(4-pentylcyclohexyl) phenyl)ethyl)benzene |
| 53 | 1-trifluoromethyl-4-(2-(2-fluoro-4-(4-hexylcyclohexyl) phenyl)ethyl)benzene |
| 54 | 1-trifluoromethyl-4-(2-(2-fluoro-4-(4-heptylcyclohexyl) phenyl)ethyl)benzene |
| 55 | 1-trifluoromethoxy-4-(2-(2-fluoro-4-(4-propylcyclohexyl) phenyl)ethyl)benzene |
| 56 | 1-trifluoromethoxy-4-(2-(2-fluoro-4-(4-butylcyclohexyl) phenyl)ethyl)benzene |
| 57 | 1-trifluoromethoxy-4-(2-(2-fluoro-4-(4-pentylcyclohexyl) phenyl)ethyl)benzene |
| 58 | 1-trifluoromethoxy-4-(2-(2-fluoro-4-(4-hexylcyclohexyl) phenyl)ethyl)benzene |
| 59 | 1-trifluoromethoxy-4-(2-(2-fluoro-4-(4-heptylcyclohexyl) phenyl)ethyl)benzene |
| 60 | 1-trifluoromethyl-2-fluoro-4-(2-(2-fluoro-4-(4-propylcyclohexyl)penyl)ethyl)benzene |
| 61 | 1-trifluoromethyl-2-fluoro-4-(2-(2-fluoro-4-(4-butylcyclohexyl)penyl)ethyl)benzene |
| 62 | 1-trifluoromethyl-2-fluoro-4-(2-(2-fluoro-4-(4-pentylcyclohexyl)penyl)ethyl)benzene |
| 63 | 1-trifluoromethyl-2-fluoro-4-(2-(2-fluoro-4-(4-hexylcyclohexyl)penyl)ethyl)benzene |
| 64 | 1-trifluoromethyl-2-fluoro-4-(2-(2-fluoro-4-(4-heptylcyclohexyl)penyl)ethyl)benzene<br>C - I point: 43.8° C. |
| 65 | 1-trifluoromethoxy-2-fluoro-4-(2-(2-fluoro-4-(4-butylcyclohexyl)phenyl)ethyl)benzene |
| 66 | 1-trifluoromethoxy-2-fluoro-4-(2-(2-fluoro-4-(4-pentylcyclohexyl)phenyl)ethyl)benzene |
| 67 | 1-trifluoromethoxy-2-fluoro-4-(2-(2-fluoro-4-(4-hexylcyclohexyl)phenyl)ethyl)benzene |
| 68 | 1-trifluoromethoxy-2-fluoro-4-(2-(2-fluoro-4-(4-heptylcyclohexyl)phenyl)ethyl)benzene |
| 69 | 1-trifluoromethyl-2,6-difluoro-4-(2-(2-fluoro-4-(4-propylcyclohexyl)phenyl)ethyl)benzene |
| 70 | 1-trifluoromethyl-2,6-difluoro-4-(2-(2-fluoro-4-(4-butylcyclohexyl)phenyl)ethyl)benzene |
| 71 | 1-trifluoromethyl-2,6-difluoro-4-(2-(2-fluoro-4-(4-pentylcyclohexyl)phenyl)ethyl)benzene |
| 72 | 1-trifluoromethyl-2,6-difluoro-4-(2-(2-fluoro-4-(4-hexylcyclohexyl)phenyl)ethyl)benzene |
| 73 | 1-trifluoromethyl-2,6-difluoro-4-(2-(2-fluoro-4-(4-heptylcyclohexyl)phenyl)ethyl)benzene |

| No. | |
|---|---|
| 74 | 1-trifluoromethoxy-2,6-difluoro-4-(2-(2-fluoro-4-(4-propylcyclohexyl)phenyl)ethyl)benzene |
| 75 | 1-trifluoromethoxy-2,6-difluoro-4-(2-(2-fluoro-4-(4-butylcyclohexyl)phenyl)ethyl)benzene |
| 76 | 1-trifluoromethoxy-2,6-difluoro-4-(2-(2-fluoro-4-(4-pentylcyclohexyl)phenyl)ethyl)benzene |
| 77 | 1-trifluoromethoxy-2,6-difluoro-4-(2-(2-fluoro-4-(4-hexylcyclohexyl)phenyl)ethyl)benzene |
| 78 | 1-trifluoromethoxy-2,6-difluoro-4-(2-(2-fluoro-4-(4-heptylcyclohexyl)phenyl)ethyl)benzene |

Further, according to the method in Example 3, the following compounds (compound Nos. 79 to 84) of the third group were prepared.

79

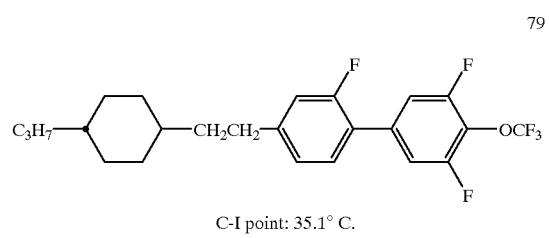

C-I point: 35.1° C.

80

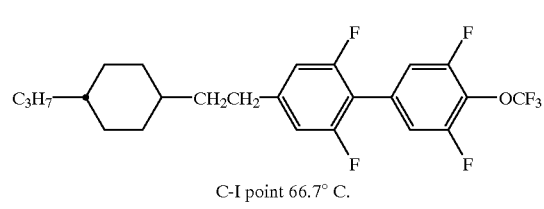

C-I point 66.7° C.

81

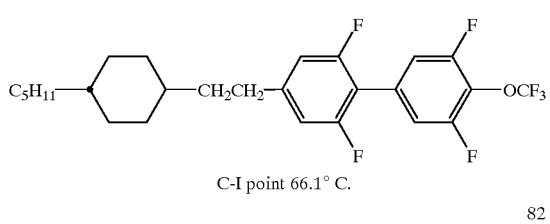

C-I point 66.1° C.

82

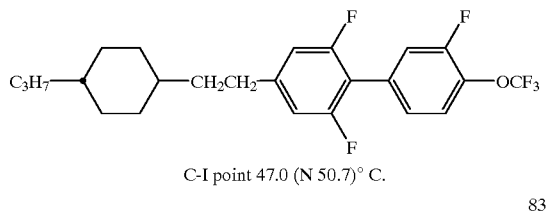

C-I point 47.0 (N 50.7)° C.

83

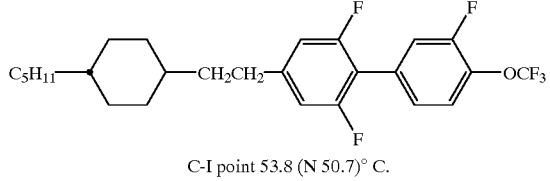

C-I point 53.8 (N 50.7)° C.

84

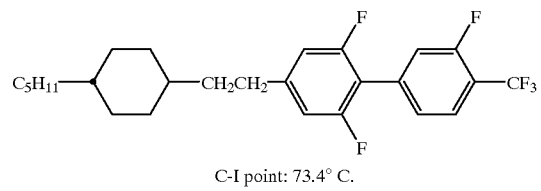

C-I point: 73.4° C.

Example 5 (Use Example 1)

Liquid crystal composition A comprising the following compounds was prepared:

4-(4-propylcyclohexyl)benzonitrile 24% by weight
4-(4-pentylcyclohexyl)benzonitrile 36% by weight
4-(4-heptylcyclohexyl)benzonitrile 25% by weight
4-(4-propylphenyl)benzonitrile 15% by weight Liquid crystal composition A had the following physical parameters:

Clearing point: 72.4° C.
$\Delta\epsilon$: 11.0
$\Delta n$: 0.137
Viscosity at 20° C.: 27.0 mPa·s
$V_{th}$ at cell thickness of 9 μm: 1.78 V Liquid crystal composition A in an amount of 85% by weight was mixed with 15% by weight of 1-trifluoromethoxy-2-fluoro-4-(2-(4-propylcyclohexyl)ethyl)benzene (Compound No. 1) of the compound of the present invention obtained in Example 1 to produce liquid crystal composition A 1-1. The composition A 1-1 had the following physical parameters:

Clearing point: 49.3° C.
$\Delta\epsilon$: 10.5 (extrapolation value: 7.7)
$\Delta n$: 0.117 (extrapolation value: 0.004)
Viscosity at 20° C: 24.8 mPa·s (extrapolation value: 12.3 mPa·s)
$V_{th}$ at cell thickness of 8.7 μm: 1.35 V
VHR at 100° C.: 99.8%

While the composition A 1-1 was left in a freezer at -20° C. for 60 days, precipitation of crystals was not noticed.

Example 6 (Use Example 2)

Liquid crystal composition A 1-2 was obtained in the same manner as in Example 5 except that 1-trifluoromethyl-2-fluoro-4-(2-(4-pentylcyclohexyl)ethyl)benzene (Compound No. 3) was used in place of Compound No. 1. The composition A 1-2 had the following physical parameters:

$\Delta\epsilon$: 10.6
$\Delta n$: 0.120
Viscosity at 20° C.: 25.2 mPa·s (extrapolation value: 19.6 mPa·s)

Example 7 (Use Example 3)

Liquid crystal composition A 2-1 was obtained in the same manner as in Example 5 except that 1-trifluoromethoxy- 2-fluoro-4-(2-(4-(2-(4-propylcyclohexyl)ethyl)cyclohexyl)ethyl)benzene (Compound No. 19) was used in place of Compound No. 1. The composition A 2-1 had the following physical parameters:

Δε: 10.4
Δn: 0.128
Viscosity at 20° C.: 25.9 mPa·s
$V_{th}$: 1.74 V

Example 8 (Use Example 4)

Liquid crystal composition A 2-2 was obtained in the same manner as in Example 5 except that 1-trifluoromethyl-2,6-difluoro-4-(2-(4-(2-(4-propylcyclohexyl)ethyl)cyclohexyl) ethyl)benzene (Compound No. 29) was used in place of Compound No. 1. The composition A 2-2 had the following physical parameters:

Δε: 11.6
Δn: 0.127
Viscosity at 20° C.: 35.0 mPa·s
$V_{th}$: 1.70 V

Example 9 (Use Example 5)

Liquid crystal composition A 3-1 was obtained in the same manner as in Example 5 except that 4'-(2-(4-propylcyclo-hexyl)ethyl)-3-fluoro-4-trifluoromethylbiphenyl (Compound No. 40) was used in place of Compound No. 1. The composition A 3-1 had the following physical parameters:

Δε: 11.3
Δn: 0.137
Viscosity at 20° C.: 29.6 mPa·s (extrapolation value: 48.6 mPa·s)
$V_{th}$: 1.74 V Example 10 (Use Example 6)

Liquid crystal composition A 4-1 was obtained in the same manner as in Example 5 except that 1-trifluoromethoxy-2-fluoro-4-(2-(2-fluoro-4-(4-propylcyclohexyl)phenyl)ethyl)benzene (Compound No. 49) was used in place of Compound No. 1. The composition A 4-1 had the following physical parameters:

Δε: 11.1
Δn: 0.139
Viscosity at 20° C. (extrapolation value): 37.4 mPa·s

Examples 11 to 16 (Use Examples 7 to 12)

Each of the compounds (compound Nos. 79 to 84) obtained in Example 4 in an amount of 15% by weight was mixed with 85% by weight of the liquid crystal composition A described in Example 5, respectively, to obtain six kinds of liquid crystal compositions, and physical parameters of the compositions were determined to obtain the properties, as extrapolation value, of the compounds as shown below:

|  | N-I point (° C.) | Δε | Δn | Viscosity at 20° C. (mPa · s) |
| --- | --- | --- | --- | --- |
| Compound (Compound No. 79) | 40.4 | 19.7 | 0.113 | 56.5 |
| Compound (Compound No. 80) | 25.0 | 24.3 | 0.097 | 62.0 |
| Compound (Compound No. 81) | 35.7 | 23.0 | 0.104 | 67.3 |
| Compound (Compound No. 82) | 36.4 | 18.3 | 0.104 | 44.0 |
| Compound (Compound No. 83) | 43.7 | 18.3 | 0.110 | 41.9 |
| Compound (Compound No. 84) | 26.4 | 23.0 | 0.110 | 64.6 |

Comparative Example 1

As examples of comparative compounds having a structure close to that of a compound (Compound No. 3) of the present invention included in the first group, a compound expressed by formula (c) (Comparative compound 1) described in Laid-open WO Japanese Patent Publication No. Sho 63-503226, a compound expressed by formula (d) (Comparative compound 2) described in Laid-open Japanese Patent Publication No. Hei 2-111734, and a compound expressed by formula (e) (Comparative compound 3), described in Laid-open Japanese Patent Publication No. Sho 61-207347, each of the publications are mentioned above, were selected, and their physical parameters (clearing point (C - I point), viscosity obtained by extrapolation from the liquid crystal composition prepared by the method mentioned below), and Δε of the liquid crystal composition containing the compound were determined.

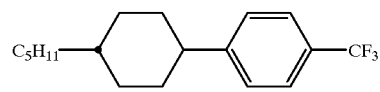

(c)

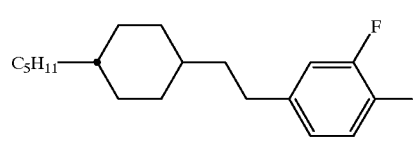

(d)

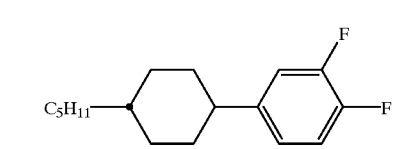

(e)

Preparation of the liquid crystal compositions were conducted in the same way as in Example 6 except that one of the Comparative compounds mentioned above was used in place of the Compound No. 3 to obtain Comparative liquid crystal compositions B 1-1, B 1-2, and B 1-3, respectively.

Results were as follows (the results for Compound No. 3 and liquid crystal composition A 1-2 (Example 6) are shown below together):

|  | Clearing point (° C.) | Extrapolated viscosity (mPa · s) |  | Δε |
| --- | --- | --- | --- | --- |
| Compound of the present invention (Compound No. 3) | 21.4 | 19.6 | A 1-2 | 10.6 |
| Comparative compound 1 | 10 | 20.8 | B 1-1 | 8.3 |
| Comparative compound 2 | -30 | -8.2 | B 1-2 | 10.9 |
| Comparative compound 3 | 0 | -12.2 | B 1-3 | 10.9 |

From the results, the followings can be seen:

With respect to Compound No. 3 of the present invention, lowering of clearing point or increase of viscosity by extrapolation method is not observed, and the compound exhibits an extremely large Δε, caused by the fact that 1,2-ethylene group is introduced as bonding group at the center of the molecule, despite of the fact that the compound has fluorine atom as substituent at a side position compared with Comparative compound 1.

Effect by the introduction of 1,2-ethylene group contradicts technological old common sense. For example, it contradicts the knowledge in prior art that Comparative compound 2 to which 1,2-ethylene group was introduced will be lower in clearing point and will be larger in increase of viscosity by extrapolation method than Comparative compound 3 to which 1,2-ethylene group was not introduced. This is a really surprising fact.

Comparative Example 2

As comparative compound having a structure close to that of a compound (Compound No. 19) of the present invention included in the second group, a compound in which three rings are linked in a straight line (Comparative compound 4) described in Laid-open Japanese Patent Publication No. Hei 2-501311 mentioned above and expressed by formula (b) wherein n is 3, and particularly expressed by formula (f) was selected.

Its phase transition temperature was as follows:

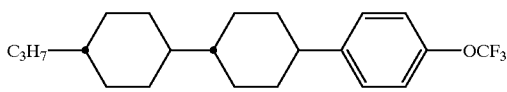

(f)

This Comparative compound 4 clearly exhibited a strong smectic property. Thus, when this compound was used as a component, the liquid crystal composition to be obtained unpreferably develops a smectic phase at low temperatures. In contrast, a compound (Compound No. 19) of the present invention to which two 1,2-ethylene groups were introduced as central bonding group does not exhibit a smectic phase but shows only a nematic phase (reference is made to Example 2), and thus the compound of the present invention does not have such a defects as of Comparative compound.

Comparative Example 3

As comparative compound having the same structure as a compound (Compound No. 40) of the present invention included in the third group except that the position where hydrogen atom is substituted with fluorine atom was changed from a position on a terminal phenylene to a position on the central phenylene, a compound (Comparative compound 5) disclosed in Liq. Cryst., 18 (4), 665 (1995) and specifically expressed by formula (g) was selected.

Physical parameters of the compound, and Δε and Δn of a liquid crystal composition (B 3-1) containing the comparative compound were determined in the same way as in Comparative Example 1. Results were as follows:

Clearing point: 80.4° C.
Viscosity at 20° C. (extrapolation value): 52.0 mPa·s
Δε: 11.0
Δn: 0.138

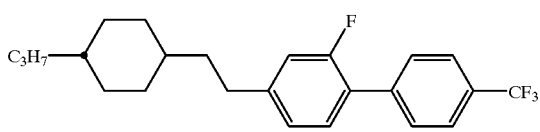

(g)

From this comparative example, it can be seen that the compound (Compound No. 40) of the present invention has a clearing point as large as about 8° C. higher than Comparative compound 5 and has a low viscosity. Also, from another investigation, it has been found that Compound No. 40 has a small temperature dependency of Δε, Δn, and viscosity, particularly has a small increase in viscosity at low temperatures, and has an excellent miscibility with other liquid crystalline compounds.

Comparative Example 4

As comparative compound having the same structure as a compound (Compound No. 49) of the present invention included in the fourth group except that the position where hydrogen atom is substituted with fluorine atom was changed from a position on a terminal phenylene to a position on the central phenylene, a compound (Comparative compound 6) disclosed in Liq. Cryst., 18 (4), 665 (1995) and specifically expressed by formula (k) was selected.

Physical parameters of the compound, and Δε and Δn of a liquid crystal composition (B 4-1) containing the comparative compound were determined in the same way as in Comparative Example 1. Results were as follows:

Clearing point: 43° C.
Viscosity at 20° C. (extrapolation value): 52.0 mPa·s
Δε: 11.0
Δn: 0.138

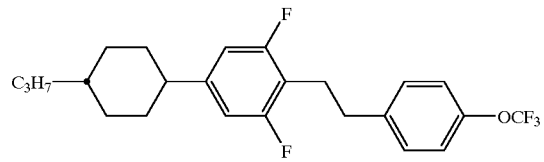

(k)

From this comparative example, it can be seen that the compound (Compound No. 49) of the present invention has. about the same or higher clearing point, Δε, and Δn compared with Comparative compound 6, and particularly has a low viscosity. Also, from another investigation, it has been found that Compound No. 49 has a small temperature dependency of each of Δε, Δn, and viscosity, and has an excellent miscibility with other liquid crystalline compounds.

We claim:

1. A liquid crystalline compound expressed by general formula (1)

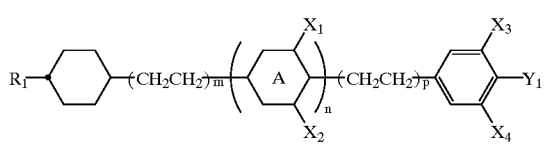

(1)

wherein $R_1$ represents an alkyl group having 1 to 10 carbon atoms, ring A represents 1,4- cyclohexylene, $X_1$ and $X_2$ both represent hydrogen atom, $X_3$ represents fluorine atom, $X_4$ represents hydrogen atom or fluorine atom, $Y_1$ represents $CF_3$ or $OCF_3$, and m, n and p are all 1.

2. A liquid crystal compositions containing at least one liquid crystalline compound defined in claim 1.

3. A liquid crystal composition containing, as a first compound, at least one liquid crystalline compound defined in claim 1, and containing, as a second component, at least one compound selected from the group of the compounds expressed by any one of general formulas (2), (3), and (4) expressed by any one of general formulas (5), (6), (7), (8), and (9)

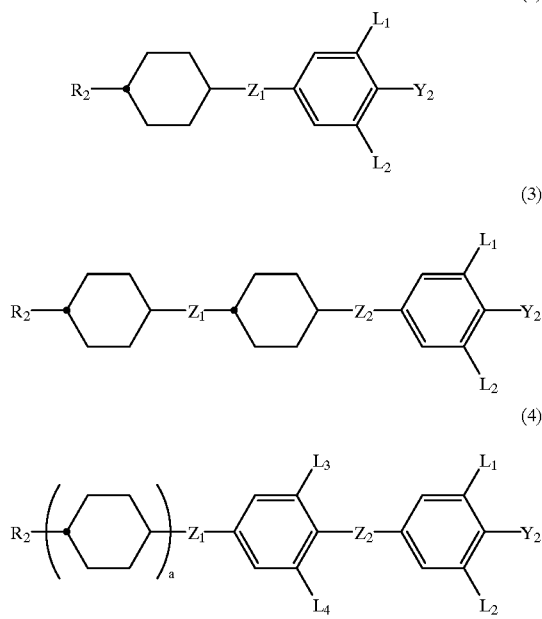

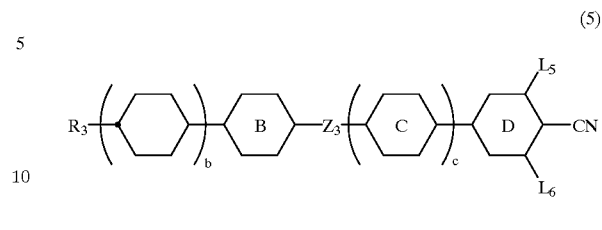

wherein $R_2$ represents an alkyl group having 1 to 10 carbon atoms, $Y_2$ represents fluorine atom, chlorine atom, $OCF_3$, $OCF_2H$, $CF_3$, $CF_2H$, or $CFH_2$, $L_1$, $L_2$, $L_3$, and $L_4$ represent, independently with one another, hydrogen atom or fluorine atom, $Z_1$ and $Z_2$ represent, independently with each other, —$(CH_2)_2$—, —CH=CH—, or a covalent bond, and a is 1 or 2.

4. A liquid crystal composition containing, as a first compound at least one liquid crystalline compound defined in claim 1, and containing, as a second component, at least one compound selected from the group of the compounds wherein $R_3$ represents fluorine atom, an alkyl group having 1 to 10 carbon atoms, or an alkenyl group having 2 to 10 carbon atoms, any methylene group in the alkyl group or alkenyl group may be replaced by oxygen atom provided that in no case two or more methylene groups are continually replaced by oxygen atom; ring B represents 1,4-cyclohexylene, 1,4-phenylene, or 1,3-dioxane-2,5-diyl, ring C represents 1,4-cyclohexylene, 1,4-phenylene, or pyrimidine-2,5-diyl, ring D represents 1,4-cyclohexylene or 1,4-phenylene, $Z_3$ represents —$(CH_2)_2$—, —COO—, or a covalent bond, $L_5$ and $L_6$ represent, independently with each other, hydrogen atom or fluorine atom, and b and c are, independently with each other, 0 or 1,

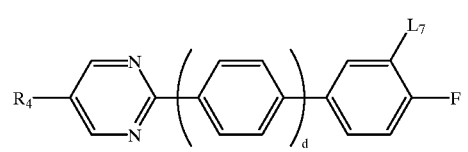

wherein $R_4$ represents an alkyl group having 1 to 10 carbon atoms, $L_7$ represents hydrogen atom or fluorine atom, and d is 0 or 1,

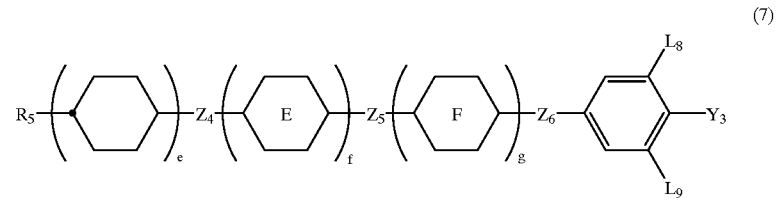

wherein $R_5$ represents an alkyl group having 1 to 10 carbon atoms, ring E and ring F represent, independently with each other, 1,4-cyclohexylene or 1,4-phenylene, $Z_4$ and $Z_5$ represent, independently with each other, —COO— or a covalent bond, $Z_6$ represents —COO— or —C≡C—, $L_8$ and $L_9$ represent, independently with each other, hydrogen atom or fluorine atom, $Y_3$ represents fluorine atom, $OCF_3$, $OCF_2H$, $CF_3$, $CF_2H$, or $CFH_2$ provided that when $Y_3$ represents $OCF_3$, $OCF_2H$, $CF_3$, $CF_2H$, or $CFH_2$, both $L_8$ and $L_9$ represent hydrogen atom; and all of e, f, and g are, independently with one another, 0 or 1,

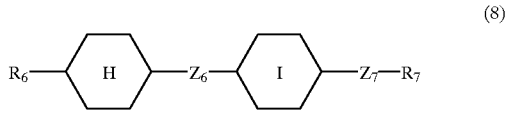

wherein $R_6$ and $R_7$ represent, independently with each other, an alkyl group having 1 to 10 carbon atoms or an alkenyl group having 2 to 10 carbon atoms, any methylene group in either the alkyl group and alkylene group may be replaced by oxygen atom provided that in no case two or more methylene groups are continually replaced by oxygen atom; ring H represents 1,4-cyclohexylene, 1,4-phenylene, or pyrimidine-2,5-diyl, ring I represents 1,4-cyclohexylene or 1,4-phenylene, $Z_6$ represents —C≡C—, —COO—, —(CH$_2$)$_2$—, —CH=CH—C≡C—, or a covalent bond, and $Z_7$ represents —COO— or a covalent bond,

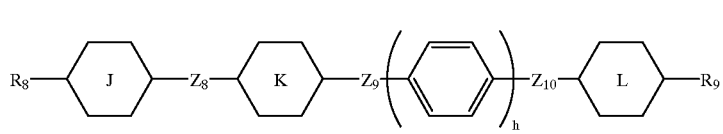

(9)

wherein $R_8$ and $R_9$ represent, independently with each other, an alkyl group having 1 to 10 carbon atoms or an alkenyl group having 2 to 10 carbon atoms, any methylene group in either the alkyl group and alkylene group may be replaced by oxygen atom provided that in no case two or more methylene groups are continually replaced by oxygen atom; ring J represents 1,4-cyclohexylene, 1,4-phenylene, or pyrimidine-2,5-diyl, ring K represents 1,4-cyclohexylene, 1,4-phenylene one or more hydrogen atoms on the ring of which may be replaced by fluorine atom, or pyrimidine-2,5-diyl, ring L represents 1,4-cyclohexylene or 1,4-phenylene, $Z_8$ and $Z_{10}$ represent, independently with each other, —COO—, —(CH$_2$)$_2$—, or a covalent bond, $Z_9$ represents —CH=CH—, —C≡C—, —COO—, or a covalent bond, and h is 0 or 1.

5. A liquid crystal composition containing, as a first component, at least one liquid crystalline compound defined in claim 1, containing, as a part of a second component, at least one compound selected from the group of the compounds expressed by any one of general formulas (2), (3), and (4) defined in claim 3, and containing, as other part of the second component, at least one compound selected from the group of the compounds expressed by any one of general formulas (5), (6), (7), (8), and (9) defined in claim 4.

6. A liquid crystal display device composed by using a liquid crystal composition defined in claim 2.

7. A liquid crystal display device composed by using a liquid crystal composition defined in claim 3.

8. A liquid crystal display device composed by using a liquid crystal composition defined in claim 4.

9. A liquid crystal display device composed by using a liquid crystal composition defined in claim 5.

* * * * *